(12) United States Patent
Maggiore

(10) Patent No.: US 11,359,172 B2
(45) Date of Patent: Jun. 14, 2022

(54) UPSTREAM AND DOWNSTREAM PROCESSING WITHIN SINGLE-USE CONTAINERS

(71) Applicant: Sartorius Stedim Biotech GmbH, Goettingen (DE)

(72) Inventor: Frank Maggiore, Port Jefferson, NY (US)

(73) Assignee: Sartorius Stedim Biotech GmbH, Goettingen (DE)

( * ) Notice: Subject to any disclaimer, the term of this patent is extended or adjusted under 35 U.S.C. 154(b) by 32 days.

(21) Appl. No.: 15/672,559

(22) Filed: Aug. 9, 2017

(65) Prior Publication Data

US 2019/0048303 A1 Feb. 14, 2019

(51) Int. Cl.
| | | |
|---|---|---|
| *C12M 1/26* | (2006.01) | |
| *C12M 3/00* | (2006.01) | |
| *C12M 1/00* | (2006.01) | |
| *B67D 3/00* | (2006.01) | |

(52) U.S. Cl.
CPC .............. *C12M 1/26* (2013.01); *B67D 3/0012* (2013.01); *B67D 3/0022* (2013.01); *C12M 23/14* (2013.01); *C12M 23/28* (2013.01); *C12M 23/44* (2013.01); *C12M 23/52* (2013.01); *B01L 2200/0631* (2013.01); *B01L 2400/0409* (2013.01)

(58) Field of Classification Search
CPC ..... B01L 2200/0631; B01L 2400/0409; B67D 3/0012; B67D 3/0022; C12M 1/26; C12M 23/14; C12M 23/26; C12M 23/28; C12M 23/44; C12M 23/55; C12M 23/52

USPC ........................................................ 435/289.1
See application file for complete search history.

(56) References Cited

U.S. PATENT DOCUMENTS

| | | | |
|---|---|---|---|
| 2002/0055166 A1* | 5/2002 | Cannon | C12M 23/42 435/286.5 |
| 2005/0054086 A1 | 3/2005 | Ophardt | |
| 2009/0311776 A1* | 12/2009 | Kelly, Jr. | C12M 23/28 435/289.1 |

(Continued)

FOREIGN PATENT DOCUMENTS

| | | |
|---|---|---|
| JP | 2005-80662 | 3/2005 |
| JP | 2012-217436 | 11/2012 |
| JP | 2014-530094 | 11/2014 |

OTHER PUBLICATIONS

Singapore Written Opinion dated Aug. 19, 2021.
Korean Office Action dated Aug. 5, 2021.

*Primary Examiner* — Liban M Hassan
(74) *Attorney, Agent, or Firm* — Gerald E. Hespos; Michael J. Porco

(57) ABSTRACT

A single-use chamber comprising a primary subchamber containing at least one primary component configured to perform an operation comprising at least one of generation and handling of a biological material; and a secondary subchamber containing at least one of a connection to equipment external to the single-use chamber and a secondary component, wherein the external equipment and the secondary component are configured to support the operation of the at least one primary component; wherein the primary subchamber and the secondary subchamber are configured to be connected to each other so that the at least one primary component is operatively coupled to at least one of the connection and the secondary component.

4 Claims, 8 Drawing Sheets

(56) References Cited

U.S. PATENT DOCUMENTS

| | | |
|---|---|---|
| 2010/0159577 A1 | 6/2010 | Tokumaru |
| 2010/0230950 A1* | 9/2010 | Williams ................ F16L 37/30 |
| | | 285/38 |
| 2011/0201100 A1 | 8/2011 | Proulx et al. |
| 2011/0217690 A1* | 9/2011 | Niazi ....................... C12Q 3/00 |
| | | 435/3 |
| 2012/0100605 A1* | 4/2012 | Kauling ............. B01F 11/0002 |
| | | 435/325 |
| 2013/0115588 A1* | 5/2013 | Davis .................... C12M 23/28 |
| | | 435/3 |
| 2014/0349385 A1 | 11/2014 | Erdenberger et al. |
| 2015/0151892 A1* | 6/2015 | Corten .................... B67D 7/08 |
| | | 366/273 |
| 2016/0114935 A1* | 4/2016 | Ronnholm ............. B65D 11/20 |
| | | 366/314 |

* cited by examiner

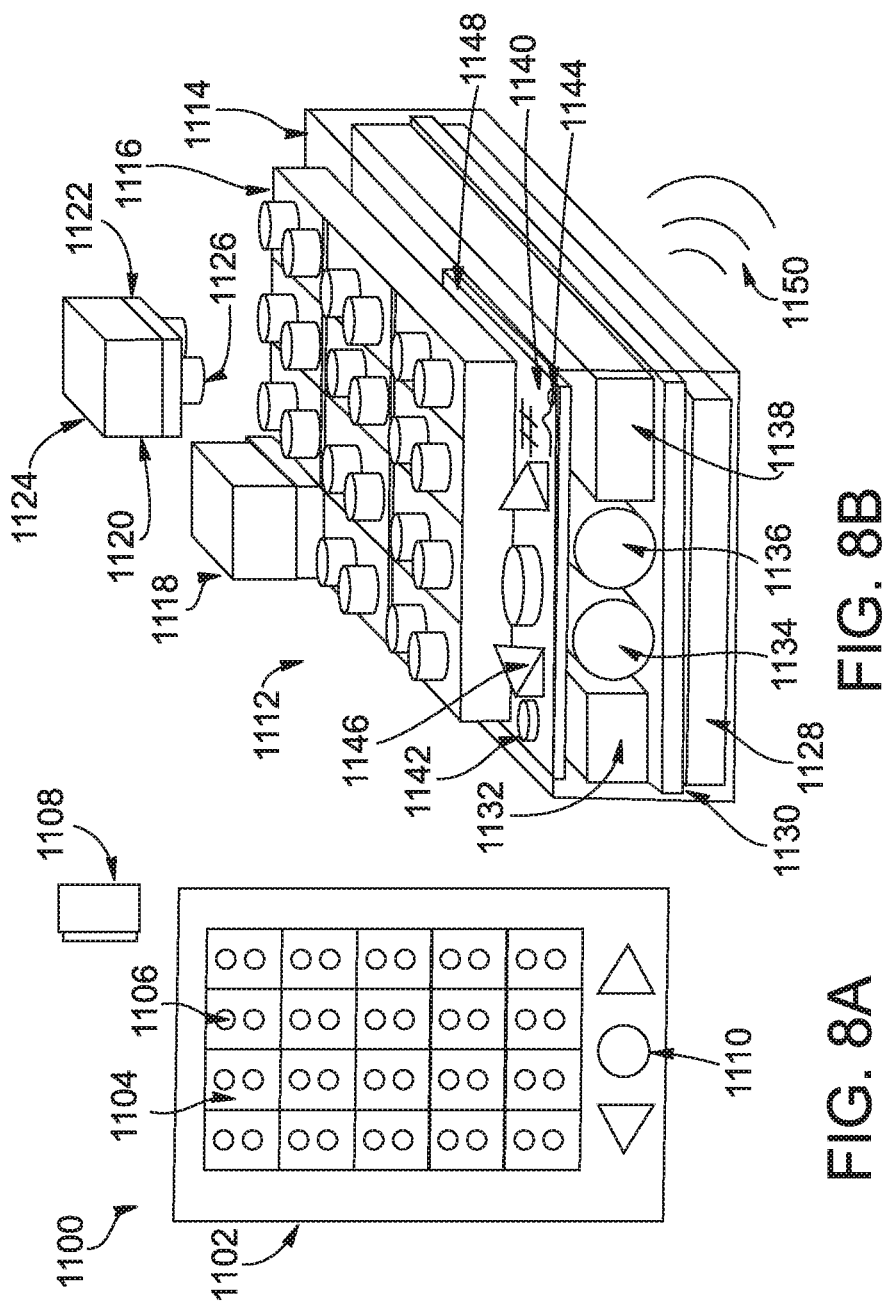

UPSTREAM AND DOWNSTREAM PROCESSING WITHIN SINGLE-USE CONTAINERS

BACKGROUND

Field of the Invention

The application relates to a single-use container to perform upstream and/or downstream processing and to a network of such single-use containers, as well as to a container assembly comprising such a single-use container together with supporting equipment.

Description of the Related Art

There are many setups, such as biopharmaceutical, pharmaceutical, laboratory, chemical, food and beverage, and industrial setups, that require a sterile environment as well as a sterile equipment in order to prevent any contamination of the products.

Exemplarily, in the biopharmaceutical field the sterile manufacture of drug products requires large-scale manufacturing facilities and large upfront equipment costs, as well as that operations be performed in a classified area. There is, thus, a need for a simplified and cheaper system for e.g. the manufacturing of drug products, particularly for personalized medicine processes and manufacturing, which can be deployed at a benchtop scale while being at the same time equally effective and safe as conventional production systems.

SUMMARY

According to one aspect, a single-use chamber is provided. The single-use chamber comprises the following:

a primary subchamber containing at least one primary component configured to perform an operation comprising at least one of generation and handling of a biological material; and a secondary subchamber containing at least one of a connection to equipment external to the single-use chamber and a secondary component, wherein the external equipment and the secondary component are configured to support the operation of the at least one primary component;

wherein the primary subchamber and the secondary subchamber are configured to be connected to each other so that the at least one primary component is operatively coupled to at least one of the connection and the secondary component.

According to another aspect, a container assembly is provided. The container assembly comprises the following:

an enclosure configured to accommodate at least one single-use chamber for performing an operation comprising at least one of generation and handling of a biological material, the enclosure comprising at least one supporting equipment module;

wherein the at least one supporting equipment module is configured to be operatively coupled to the at least one single-use chamber to support the operation of the at least one single-use chamber, and wherein a modular arrangement of the at least one supporting equipment module and of the at least one single-use chamber is selectively mountable in one configuration of a plurality of possible configurations.

According to a further aspect, a single-use manufacturing system is provided. The single-use manufacturing system comprises at least one single-use chamber containing a plurality of components configured to perform the entire upstream and downstream processing of biological material.

Details of exemplary embodiments are set forth below with reference to the exemplary drawings. Other features will be apparent from the description, the drawings, and from the claims. The drawings should be understood as exemplary rather than limiting, as the scope of the invention is defined by the claims.

BRIEF DESCRIPTION OF THE DRAWINGS

FIGS. 8A and 8B illustrate an example of a miniaturized container assembly for single-use containers.

DETAILED DESCRIPTION

Figures 1A, 1B:
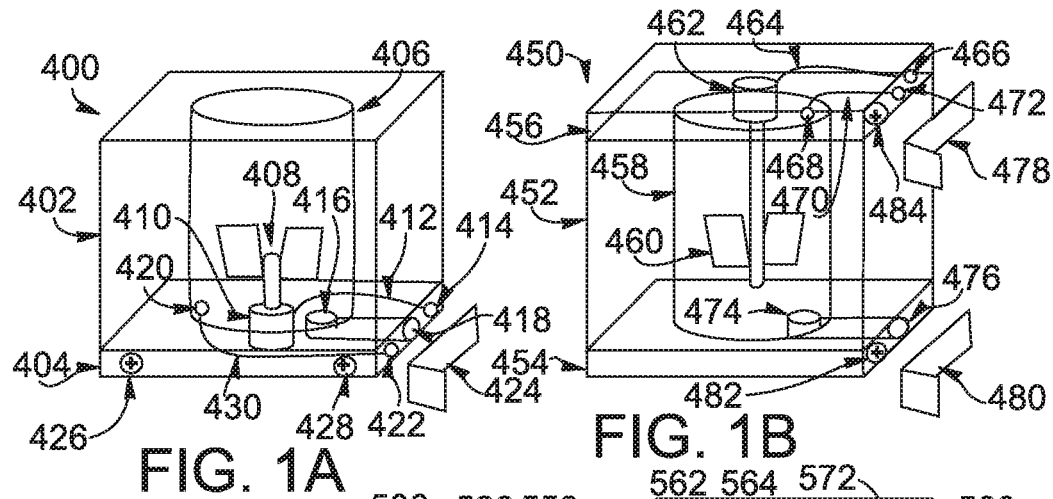
FIGS. 1A-1D illustrate multiple examples of the construction of a single-use container comprising subchambers that is suitable to form a network of single-use containers.

In the following text, a detailed description of examples will be given with reference to the drawings. It should be understood that various modifications to the examples may be made. In particular, one or more elements of one example may be combined and used in other examples to form new examples.

In the following the terms "single-use container" and "single-use chamber" will be used interchangeably. Further, unless specified otherwise (see secondary subchambers as discussed below), all single-use items are always sterilizable and, when used, previously sterilized.

The invention described here provides a system for the automated and customized manufacture of small to medium scale sterile drug products, i.e. for performing the whole upstream and downstream processing, without the requirement for large-scale manufacturing facilities. Upstream processing generally refers to the processes from cell cultivation until the final harvest of material. Downstream processing generally refers to purification and polishing of the harvest material. In some examples, the system may be configured to perform only downstream processing.

In particular, the system herein described comprises at least one sterile, single-use chamber that may be utilized to perform the upstream and/or downstream processing of a biological product. Biological materials may include materials comprising a biological system, such as cells, cell components, cell products, and other molecules, as well as materials derived from and/or having an effect on a biological system, such as proteins, antibodies and growth factors.

The upstream-downstream processing of a biologic material may take place within a single-use container and/or a network of single-use containers. A series of single-use chambers may be connected into a network of chambers where each chamber performs a specific task for the processing of the biological material such as cells, proteins, antibodies, viruses, etc.

A single-use container is a disposable container that is configured for a one-time use. After the single-use container has been used once, it has fulfilled its function and may be disposed of. Exemplarily, a single-use container is made of plastic, which may include but is not limited to polyamide, polycarbonate, polyethylene, polystyrene, polyethersulfone, polypropylene, polytetrafluoroethylene, polyvinyl chloride, cellulose acetate and/or ethyl vinyl acetate. In one example, the single-use container may be rigid, i.e. its shape may not be modified. In another example, the single-use container may have flexible walls, i.e. it may be capable of changing its shape without breaking. The material of the single-use container can be chosen so that the single-use system is easily sterilizable, as is the case for plastic.

Exemplarily, the single-use chambers used for processing biological material may comprise two or more subchambers. A single-use chamber may comprise a primary subchamber containing at least one primary component configured to perform an operation comprising at least one of generation and handling of a biological material. The primary component may be for example a bioreactor or a receptacle for one or more of the following assemblies: a mixing assembly, a centrifugation assembly, a filtration assembly, a storage assembly, a crossflow purification and concentration assembly and a dispensing assembly.

Further, the single-use chamber may comprise a secondary subchamber containing at least one of a connection to equipment external to the single-use chamber and a secondary component, wherein the external equipment and the secondary component are configured to support the operation of the at least one primary component. The equipment external to the single-use chamber may comprise supplying units (of power, water, gas, etc.) and/or waste disposal units. It may additionally or alternatively comprise other single-use chambers. The connection may comprise wires, tube lines and/or cables.

The primary subchamber, being the subchamber hosting the actual operation performed by the single-chamber, may have a larger volume than the second subchamber.

It may be worth noting that the concept of subchamber is intrinsically different from the concept of chamber. The single-use chambers used e.g. to form a network of chambers work in cooperation to perform a series of operations on biological material that may go from producing the material to dispensing the final product generated therefrom. However, each single-use chamber may be a self-contained unit for fulfilling a specific function, although it may need to receive material from the other chambers and to receive e.g. power supply from external units. Conversely, the primary subchamber and the secondary subchamber are interdependent and may only work as a combination, i.e. they are not self-contained. The primary component in the primary subchamber may not operate at all without the necessary connections and additional components in the second subchamber which is supportive of the primary subchamber, and the content of the second subchamber may not fulfill any function independently on its own. Therefore a chamber comprising a primary subchamber and a secondary subchamber is different from a network comprising two chambers.

The primary subchamber and the secondary subchamber may be connected to each other so that the at least one primary component is operatively coupled to at least one of the connection and the secondary component. In other words, the connection between the subchambers enables a coupling between the content of the primary subchamber and the content of the secondary subchamber, so that the single-use chamber may perform the operation for which it is designed. For example, an impeller in the primary subchamber may be operatively coupled to a motor in the secondary subchamber or to a connection in the secondary subchamber that leads to an external motor.

The primary subchamber and the secondary subchamber may be permanently connected to each other. Accordingly, they may be formed together and/or attached by an attachment mechanism such as heat welding, ultrasonic welding or adhesives. In other examples, the primary subchamber and the secondary subchamber may be removably connected, e.g. by means of mechanical connections involving mating means such as protrusions, coupling elements, and/or barb lock projections. For example, the subchambers may be connected to each other so that one side of the primary subchamber and one side of the secondary subchamber are in contact and overlap each other.

The primary subchamber and the second subchamber may be formed from different materials so that one has rigid walls and the other has flexible walls. Alternatively, they may be formed from the same flexible material and then one subchamber may undergo a treatment (e.g. photopolymerization) to harden the material while the other remains flexible.

All of the components and assemblies of the primary subchamber and/or the secondary subchamber may be sterilized using an approved sterilization method such as by gamma-irradiation, autoclaving, steam-in-place, or chemical sterilant. In one example, both subchambers may be sterilized using the same method. In another example, the primary subchamber and the secondary subchamber may be sterilized via different sterilization methods. In yet another example, the primary subchamber may be sterilized and the secondary subchamber may remain unsterilized. This could allow the secondary subchamber to contain components that usually cannot be part of single-use chambers because incapable of undergoing a sterilization process, such as electronic components and/or electro-mechanical components such as a motor assembly. In other words, the primary subchamber that processes the biological material may be sterilized as required, while the secondary subchamber may be not-sterilizable. This non-sterilizable subchamber may include supporting equipment such as sensors, motors, processing devices, and/or communication devices which may be unable to undergo certain forms of sterilization.

The single-use chamber may further comprise coupling means configured to aseptically couple the single-use chamber to at least one additional single-use chamber. The single-use chamber may be connected to at least one other single-use chamber either through the connection of the primary subchamber or the secondary subchamber or both. This connection between the at least two single-use chambers may be an aseptic connection where the two chambers may be at least partially fluidly connected.

The connection between the single-use chambers may be achieved by means of attachment devices for linking and holding the single-use chambers together. Examples of attachment devices include but are not limited to mating mechanical components, coupling elements, barb locks, snap-in-place projections, twist lock, Velcro®, Dual Lock™ fasteners, aseptic connectors, and/or adhesives.

The single-use chamber may further comprise a tertiary subchamber containing at least one of a connection to equipment external to the single-use chamber and a tertiary component, wherein the external equipment and the tertiary component are configured to support the operation of the at least one primary component.

FIGS. 1A-1D illustrate multiple examples of the construction of a single-use container 400, 450, 500, 550 comprising subchambers that is suitable to form a network of single-use containers.

FIG. 1A is a front view of a single-use chamber 400 comprising a primary subchamber 402 having flexible walls formed from a single-use film material and a secondary subchamber 404 having rigid walls formed from a single-use plastic material. The primary subchamber 402 may contain the primary components for the operations of the single-use chamber 400 and, thus, constitute the operating space within the single-use chamber 400. In this example the single-use chamber 400 contains at least one flexible mixing assembly receptacle 406 within the primary subchamber 402. The at least one flexible mixing assembly receptacle 406 may be a bioreactor mixing container for the growth of cells or other biological materials.

The at least one flexible mixing assembly receptacle 406 may be formed within the volume of the primary subchamber 402 and may be attached to at least one side of the primary subchamber 402. In alternative examples, the at least one flexible mixing assembly receptacle 406 may be attached to more than one side of the primary subchamber 402, including attachment at the top and bottom of the flexible assembly or from one side to another side. The flexible primary subchamber 402 and the at least one flexible mixing assembly receptacle 406 may be filled with sterile air to inflate the flexible structure and maintain a deployed state. In the deployed state the at least one flexible mixing assembly receptacle 406 may be filled with a nutrient rich media (not shown) for the purposes of generating a biological material. A mixing device internal to the at least one flexible mixing assembly receptacle 406, which in this example is at least one impeller 408, may be utilized to thoroughly mix and/or maintain biological materials in suspension.

The secondary subchamber 404 may contain connection lines to equipment external to the single-use chamber 400, such as supplying units, other single-use chambers and/or waste disposal units, and/or secondary components to support the operation of the primary subchamber 402. The connection lines within the secondary subchamber 402 may include but are not limited to: fluid lines and piping including filling, drainage, venting and/or filtration lines; compressed gas lines and air lines; compressed fluid lines; electrical connections; power cables and wiring; data, fiber optics, and information cables; fluid and solid waste lines; mechanical connections to external equipment such as an external motor assembly with a direct connection containing sealed bearings or an extension of the motor shaft into an envelope of a shaft. The secondary components may include but are not limited to: vessels for water, media, and buffers; fluid regulating components such as valves, pumps, and manifolds; sensors and/or measurement devices; motors and other internal mechanical assemblies.

The primary subchamber 402 and/or the secondary subchamber 404 may be sterilized by utilizing the same method, may be sterilized utilizing different methods, or may not be sterilized as required. All of the components and assemblies of the primary subchamber 402 and/or the secondary subchamber 404 may be sterilized using an approved sterilization method such as by gamma-irradiation, autoclaving, steam-in-place, or chemical sterilant (such as ethylene oxide or vaporized hydrogen peroxide). Components that cannot undergo sterilization by the method selected for the primary subchamber 402 and/or the secondary subchamber 404 may be sterilized using an alternative sterilization method and aseptically connected to the primary subchamber 402 and/or the secondary subchamber 404 post-sterilization.

In this example the primary subchamber 402 and/or the secondary subchamber 404 may be sterilized as a combined assembly through gamma irradiation. In alternative examples the primary subchamber 402 may be sterilized by a chemical sterilant such as vaporized hydrogen peroxide gas and the secondary subchamber 404 may be sterilized by a different concentration of vaporized hydrogen peroxide or a different chemical sterilant such as ethylene oxide. In other examples the primary subchamber 402 may be sterilized by a chemical sterilant such as vaporized hydrogen peroxide gas and the secondary subchamber 404 may remain unsterilized.

The primary subchamber 402 may be permanently or removably attachable to the secondary subchamber 404. When the primary subchamber 402 is permanently attached to the secondary subchamber 404, they may be formed together and/or attached by an attachment mechanism such as heat welding, ultrasonic welding, radio frequency welding, coupling elements, barb locks, snap-in-place projections, twist lock, fasteners, aseptic connectors, adhesives, and/or other attachment method, or utilize an internal scaffolding or support which provides rigidity to the secondary subchamber 404. Alternatively, the primary subchamber 402 and the secondary subchamber 404 may be made from the same material and undergo some treatment process (such as by applying heat, modifying the pH, by photopolymerization, or other method) to make one portion rigid while the other remains flexible.

The at least one impeller 408 within the at least one flexible mixing assembly receptacle 406 in the primary subchamber 402 side of the single-use chamber 400 is connected to at least one motor assembly 410 within the secondary subchamber 404 through at least one connection method. The at least one connection method may include but is not limited to a direct connection containing sealed bearings, an extension of the motor shaft into an envelope of the shaft in the at least one flexible mixing assembly receptacle 406, a magnetic coupling, a superconducting magnetic coupling, and/or a fluid drive connection. In simpler examples the secondary subchamber 404 may simply house the connection to an external motor assembly external to the secondary subchamber 404 or in more complex examples the secondary subchamber may contain the complete motor assembly.

The at least one flexible mixing assembly container 406 with at least one impeller 408 may contain a plurality of impeller shapes and designs. In this example, the at least one motor assembly 410 in the rigid secondary subchamber 404 is a standalone functional motor positioned to make a connection under the at least one impeller 408 within the primary subchamber 402. The at least one motor assembly 410 may be powered through a power cable 412 positioned within the volume of the rigid secondary subchamber 404 that leads to an external connector 414. This external connector 414 may be plugged into at least one adjoining single-use chamber (not shown) utilizing an attachment mechanism that would serve as an intermediary for completing the circuit up to a power source. In another example, the external connector 414 may be positioned to plug directly into a power source and potentially serve as a power source for an intermediary connection for at least one adjoining single-use chamber (not shown).

In this example the at least one flexible mixing assembly receptacle 406 comprises at least one section of piping 416 between the primary subchamber 402 and the secondary subchamber 404. This at least one section of piping 416 allows the mixing fluid to drain into at least one outlet piping 418. In alternative examples the single-use chamber 400 may contain at least one fluid inlet line (not shown) and at least one opening (not shown) for fluid to fill the at least one flexible mixing assembly receptacle 406. The at least one section of piping 416 and at least one outlet piping 418 may contain at least one valve (not shown) that in the closed state maintains a fluid seal to keep the fluid volume within the at least one flexible mixing assembly receptacle 406 and in the open state allows the fluid from the at least one flexible mixing assembly receptacle 406 to flow through the at least one section of piping 416 and into the at least one outlet piping 418. The at least one valve may be operated by a mechanical, magnetic, pneumatic, and/or hydraulic movement, which may exemplarily be supported within the secondary subchamber 404. The at least one outlet piping 418 may be fluidly connected to at least one adjoining single-use chamber (not shown) through an external connection. The external connection may be an aseptic connection that aseptically joins at least two fluid connections, which may maintain sterility within the connected fluid lines.

At least one sensor and/or measurement device 420 may collect data internal to either the primary subchamber 402, the secondary subchamber 404, and/or the components within. In this example the at least one sensor and/or measurement device 420 is connected to and performs a measurement on the at least one flexible mixing assembly receptacle 406. The at least one sensor and/or measurement device 420 may be wireless (not shown) and/or may contain a cable 430 which transmits data and/or power to the at least one sensor and/or measurement device 420. The at least one sensor and/or measurement device 420 may transmit data and/or receive power through the cable 430, which is positioned within the volume of the rigid secondary subchamber 404 and leads to an external connector 422. The external connector 422 may be plugged into at least one adjoining single-use chamber (not shown) utilizing an attachment mechanism which would serve as an intermediary for completing the circuit for transmitting data and/or connection to a power source. Alternatively, the external connector 422 may be positioned to plug directly into a source for transmitting data and/or power as well as potentially serving as an intermediary connection for transmitting data and/or power to at least one adjoining single-use chamber (not shown).

The single-use chamber 400 may comprise an aseptic connection assembly pull tab 424 that protects the ending of the connection lines in the secondary subchamber and, once removed, allows the connection to equipment external to the single-use chamber 400, which may include one or more adjoining single-use chambers, supplying units and/or waste disposal units. The aseptic connection assembly 424 may be similar to other physical aseptic connectors, e.g. the Sartorius OPTA® aseptic connector, which utilize a sterilizing grade filter membrane to cover the connections. After the at least two components are connected, the filter membrane is removed by pulling on the pull tab, thereby forming a fluid, power, data connection between the two components. At least one seal may be selectively removed during the removal of the pull tab 242 to open the pathway between the aseptically adjoined components.

In this example the removal of the pull tab 424 may expose the external connectors 414 and 422 and the ending of the outlet piping 418, thereby allowing connection to an adjoining single-use chamber or other external unit for transmitting data, power, or fluid such as the biological material.

The single-use chamber 400 may be connected to at least one other single-use chamber (not shown) either through the connection of the primary subchamber 402 or the secondary subchamber 404 or both. This connection between the at least two single-use chambers may be an aseptic connection where the two chambers may be at least partially fluidly connected.

The connection between two single-use chambers may be achieved using at least one attachment device 426 and 428. The attachment device may be molded or attached to the primary subchamber 402 and/or the secondary subchamber 404 of the single-use chambers. According to one example, the attachment device 426 and 428 may be on the subchamber with rigid walls, such as the secondary subchamber in FIG. 1A. The at least one attachment device 426 and 428 may make at least one permanent and/or removable physical connection to link and hold the single-use chambers together. The attachment device may be on the side at which the two chambers come into contact or at a different position.

FIG. 1B is a front view of a single-use chamber 450 comprising a primary subchamber 452 with flexible walls, a secondary subchamber 454 at the bottom of the assembly and a tertiary subchamber 456 at the top of the assembly, both having rigid walls. Similarly to the primary subchamber 402 of view A, the primary subchamber 452 may contain the primary components, while the secondary subchamber 454 and tertiary subchamber 456 may contain connection lines to equipment external to the single-use chamber 450, such as supplying units, other single-use chambers and/or waste disposal units, and/or secondary components to support the operation of the primary subchamber 452. In this embodiment the rigid secondary subchamber 454 and the tertiary subchamber 456 may provide additional stability and physical protection of the flexible walled primary subchamber 452 from external punctures or mechanical tearing.

The features of the single-use chamber 450 with regard to sterilization processes and attachment between the subchambers may be the same as discussed with reference to FIG. 1A. In particular, the tertiary subchamber 456 may remain unsterilized.

Further, the single-use chamber 450 contains at least one flexible mixing assembly receptacle 458 within the primary subchamber 452 and the at least one flexible mixing assembly receptacle 458 may have the same features and function in the same way as the flexible mixing assembly receptacle 406 described for View A, unless otherwise specified. In particular, the flexible mixing assembly receptacle comprises at least one impeller 460 analogous to the impeller 408.

The only difference is that the at least one impeller 460 within the at least one flexible mixing assembly container 458 in the primary subchamber 452 is connected to at least one motor assembly 462 within the tertiary subchamber 456 through at least one connection method. In this example the impeller 460 and the impeller shaft are located in the top position and the at least one motor assembly 462, the power cable 464, and the external connection 466 are located in the rigid tertiary subchamber 456. In this example, also the at least one sensor and/or measurement device 468, the cable 470 used to transmit data and/or supply power, and the external connection 472 are located in the rigid tertiary subchamber 456.

In this example the at least one flexible mixing assembly container 458 contains at least one section of piping 474 between the primary container 452 and the secondary container 454. This at least one section of piping 474 allows the mixing fluid to drain into at least one at least one outlet piping 476, similarly to the section of piping 416 and the outlet piping 418.

The single-use chamber 450 may comprise an attachment device 482 and 484 similar to the attachment device 426 and 428 of the single-use chamber 400. The attachment device may be molded or attached to the primary subchamber 452, the secondary subchamber 454 and/or the tertiary subchamber 456. In this example, the at least one attachment device 426 and 428 may be provided partly on the rigid secondary subchamber 454 and partly on the tertiary subchambers 456 to increase the stability.

The single-use chamber 450 may comprise two aseptic connection assembly pull tabs 478 and 480, one for the secondary subchamber 454 and one for the tertiary subchamber 456.

Figures 1C, 1D:
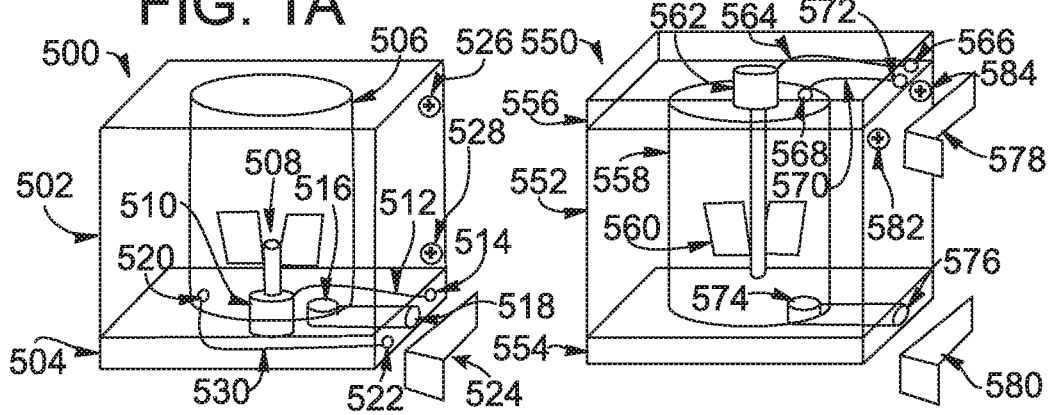

FIG. 1C is a front view of a single-use chamber 500. The single-use chamber 500 is identical to the single-use chamber 400 of View A, except for three differences. The first difference is that the rigidity of the walls is swapped between the primary subchamber and the secondary subchamber. In other words, the single-use chamber 500 comprises a primary subchamber 502 with rigid walls and a secondary subchamber 504 on the bottom of the assembly with flexible walls. The second difference is that the attachment device 526 and 528 is provided on the primary subchamber 502 and not on the secondary subchamber 504. The third difference is that the at least one sensor and/or measurement device 520 is located in the flexible secondary subchamber 504.

For the rest, the single-use chamber 500 may have the same features and function in the same way as the single-use chamber 400 described with reference to View A. In particular, the at least one mixing assembly container 506, the at least one impeller 508, the at least one motor assembly 510, the power cable 512, the external connection 514, the at least one sensor and/or measurement device 520, the cable 530, the external connection 522, the at least one section of piping 516, the at least one outlet piping 518, the aseptic connection pull tab 524 and the at least one attachment device 526 and 528 correspond to the elements with the same name in the single-use chamber 400.

FIG. 1D is a front view of a single-use chamber 550. The single-use chamber 550 is identical to the single-use chamber 450 of View B, except for two differences. The first difference is that the rigidity of the walls is swapped between the primary subchamber and the secondary/tertiary subchambers. In other words, the single-use chamber 550 comprises a primary subchamber 552 with rigid walls, a secondary subchamber 554 at the bottom of the assembly with flexible walls and a tertiary subchamber 556 at the top of the assembly with flexible walls. The second difference is that the attachment device 582 and 584 is provided on the primary subchamber 552 and not on the secondary subchamber 554 and the tertiary subchamber 556.

For the rest, the single-use chamber 550 may have the same features and function in the same way as the single-use chamber 450 described with reference to View C. In particular, the at least one mixing assembly container 558, the at least one impeller 560, the at least one motor assembly 562, the power cable 564, the external connection 566, the at least one sensor and/or measurement device 568, the cable 570, the external connection 572, the at least one section of piping 574, the at least one outlet piping 576, the aseptic connection pull tabs 578 and 580 and the at least one attachment device 582 and 584 correspond to the elements with the same name in the single-use chamber 450.

As explained above, the use of single-use chambers increases the flexibility of a manufacturing process. Including the entire biopharmaceutical drug manufacturing process, from upstream product generation via downstream purification up to the final product dispensing, within one or more sterile, single-use chambers that are discarded at the conclusion of the batch run offers a flexible platform for producing drugs on a small-to-medium scale. For example, clinical trial material or personalized medicine utilizing autologous material may be produced.

In comparison to large manufacturing facilities, smaller, more flexible, modular, and customizable single-use assemblies can be operated anywhere (office space, hospitals, clinics, etc.) with minimal resources, support, or operator involvement. This would allow for increased competition and rapid response for overcoming supply disruptions in generic drug manufacturing, promote reductions in the costs for manufacturing drugs and lead to more personalized medicine. In the paradigm of personalized medicine drug products, particularly autologous products from a patient's own cells, drug products could be manufactured on a patient to patient basis in the hospital or treatment facility with proper controls, sampling, and integrity testing, while complying with regulatory manufacturing practices.

A plurality of sterile single-use chambers may form a network where each of the chamber performs a specific task in the processing of a biological product. The single-use chambers may be connected to each other via transfer hatches and/or aseptic connectors when the chambers are unitary or they may be connected to each other via the mechanisms described with reference to FIGS. 1A-1D when the chambers contain subchambers.

The network of chambers may comprise specialized chambers for the upstream processing, including e.g. chambers containing single-use bioreactors for cell culture/fermentation as well as chambers for batch cultivation, continuous cultivation, fed-batch culture and perfusion setups. Alternatively, a separate bioreactor may be utilized to generate the biological material and be aseptically connected to the network of single-use chambers for further processing. Once the biological material is collected, it moves via a pump to another chamber for cell harvest.

The downstream processing and purification of the harvest material may require a first chamber for removal of cell debris utilizing depth filtration and/or single-use centrifugation. The biological material may be further purified through pre-filtration and sterile-filtration in another chamber, and it may undergo ultrafiltration in yet another chamber, e.g. through crossflow, diafiltration to concentrate samples, virus filtration and/or viral inactivation, membrane adsorption using an ion exchanger, chromatography or other purification methods.

From here the purified drug product may enter into another sterile chamber for the sterile dispensing of the drug product into single-use bags, bottles, syringes, or into custom 3D components such as auto-injectors, inhalers, or other delivery devices.

To summarize, the entire manufacturing process takes place within a single sterile chamber or a network of aseptically connectable sterile chambers. Such a manufacturing system may be delivered customized and pre-sterilized, requiring minimal effort on the user side for setting up and operating the system. The modularity and flexibility of the system can address the growing needs within the field of personalized medicine.

According to the exemplary embodiments of the present disclosure, setups and operation of one or more single-use chambers for the upstream and downstream processing of biological materials are described. Each of the chambers described in the following may comprise one or more subchambers as described with reference to FIG. 1, or may be a unitary chamber with no subchambers.

Figure 2:
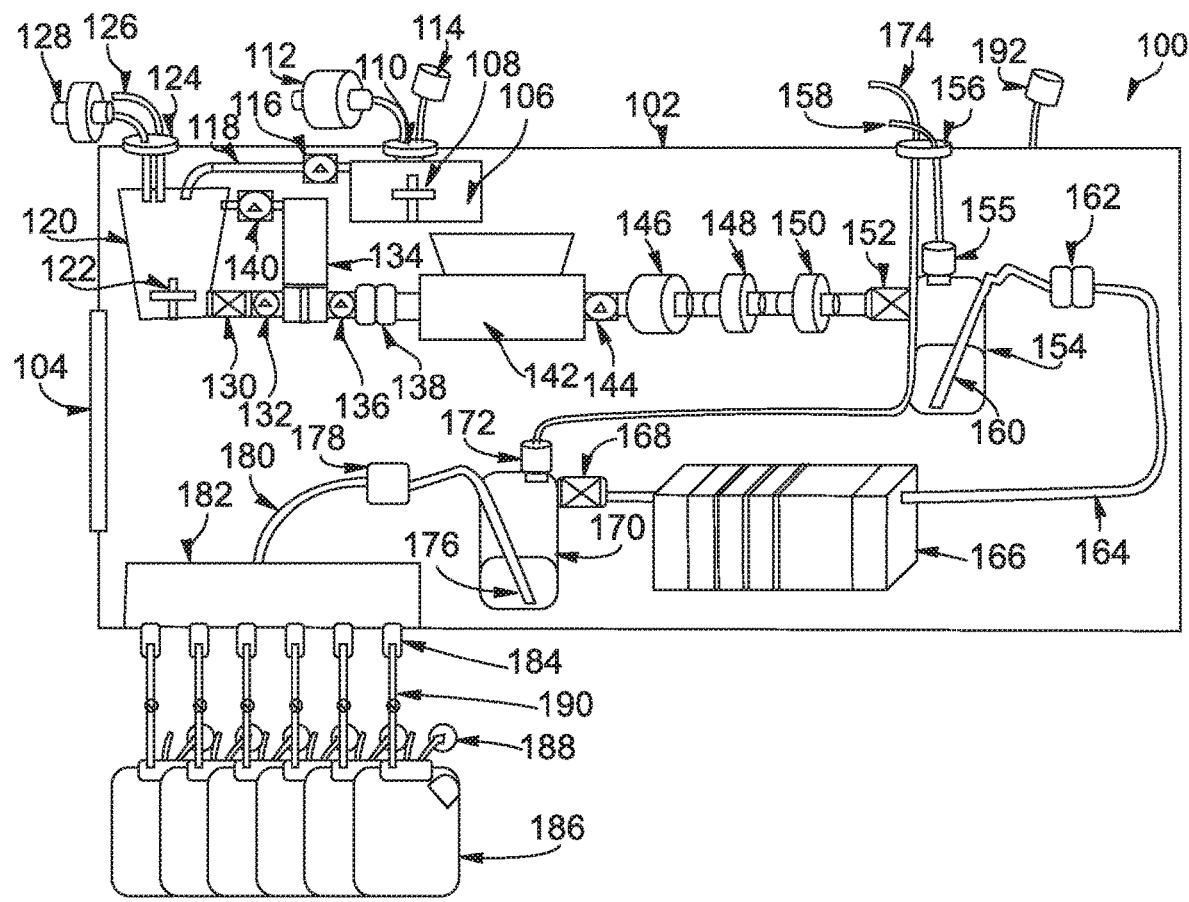
FIG. 2 illustrates an example of a manufacturing system for the upstream and downstream processing of a biological material within a single-use container.

FIG. 2 illustrates an example of a manufacturing system for the upstream and downstream processing of a biological material within a single-use container 100.

The single-use chamber 100 may comprise one or more flexible walls made from a single-use film material, one or more rigid walls made from plastic, or a combination of at least one flexible wall and at least one rigid wall. The single-use chamber 100 may contain all of the assemblies required for the processing of a biological material internal to the chamber. The necessary assemblies include but are not limited to a mixing assembly 106, a bioreactor assembly 120, a perfusion assembly 134, a centrifugation assembly 142, a filtration assembly 146, 148 and 150, a fluid storage assembly 154, a crossflow purification and concentration assembly 166, an additional fluid storage assembly 170, a dispensing assembly 182, a venting assembly 192, a pressurized gas assembly 156 and a transfer hatch assembly 104.

All of the components and assemblies of the single-use chamber 100 may be sterilized using an approved sterilization method such as by gamma-irradiation, autoclaving, steam-in-place, or chemical sterilant (such as ethylene oxide or vaporized hydrogen peroxide). In this example the single-use chamber 100 may contain a flexible film wall 102 that has undergone sterilization by gamma irradiation. Components that cannot undergo sterilization by the method selected for the single-use chamber 100 may be sterilized using an alternative sterilization method and be aseptically connected to the chamber 100.

The entire chamber 100 may be vented using at least one vent filter assembly 192, which may comprise a plurality of sterilizing and/or non-sterilizing grade vent filters. The at least one vent filter assembly 192 maintains a sterilized air space within the single-use chamber 100. Any sterilizing grade filters from the at least one vent filter assembly 192 may be integrity testable to ensure sterility within the single-use chamber 100. The entire chamber 100 may be leak testable using a leak testing device, such as a Sartocheck® 4Plus Bag Tester to perform a leak test to check for potential punctures to the body of the single-use chamber 100.

The transfer hatch assembly 104 may be utilized to add and/or remove components, units, consumables, and/or final products into or out of the single-use chamber 100. The transfer hatch assembly 104 may be aseptically connected to a sterile transfer bag for aseptically moving products out from the single-use chamber 100. Additionally or alternatively a glove assembly (not shown) may be aseptically connected to the transfer hatch assembly 104 for troubleshooting, moving stuck components internal to the single-use chamber 100 during processing, and/or for manually moving internal components around.

The at least one mixing assembly 106 may be utilized to mix media, nutrient rich broths, and buffers to support the growth of at least one biological material in the at least one bioreactor assembly 120. The mixing assembly 106 may contain at least one mixing device, such as an impeller 108, which may connect to an external motor via: a direct connection containing sealed bearings, an extension of the motor shaft into an envelope of the shaft in the single-use chamber 100, a magnetic coupling, a superconducting magnetic coupling, and/or a fluid drive connection. All other components described below that connect to an external motor may utilize one of these connections. The mixing shaft assembly with at least one impeller 108 may comprise a plurality of impeller shapes and designs and may be contained within a cell of the mixing assembly 106.

The mixing assembly 106 may comprise at least one external assembly 110 for the input of sterile material in fluid form into the cell of the mixing assembly 106 through at least one filter assembly 112 that may comprise a plurality of sterilizing and/or non-sterilizing grade filters. Additionally and/or alternatively the external assembly 110 may contain at least one aseptic connection (not shown) where powdered material may be added to the cell of the mixing assembly 106, where it is mixed with a fluid from the filter assembly 112.

At least one vent filter assembly 114, which may comprise a plurality of sterilizing and/or non-sterilizing grade vent filters, may be connected to the external assembly 110 with a length of tubing or with a plurality of aseptic connectors (not shown). The mixing assembly 106 may contain at least one valve (not shown), so that, when the valve is in an open state, the fluid sterile material may be pumped out of the cell of the mixing assembly 106 using at least one pump 116 that supplies the fluid through at least one length of tubing 118 to the at least one bioreactor assembly 120. The at least one pump 116 may connect to an external motor via one of the connection mechanisms explained above.

The at least one bioreactor assembly 120 may be utilized for batch cultivation, continuous cultivation, fed-batch culture and perfusion setups for cell culture and/or fermentation of cells, bacterial, yeasts, molds, viruses, or other biologic material for the generation of at least one biological material product.

The bioreactor assembly 120 may contain at least one mixing device, such as an impeller 122. The bioreactor assembly 120 may comprise at least one external assembly 124 for the inoculation of material aseptically into the cell of the bioreactor assembly 120 via an inoculation port 126. The bioreactor assembly 120 may contain a heating element (not shown) that may provide thermal regulation of the bioreactor for optimal cell growth. The heating element (not shown) may utilize recirculation of a heated fluid, an electric heater jacket, a heated coil, and/or forced hot air in the region of the bioreactor assembly 120. The entire single-use chamber 100 may be thermally regulated by an external assembly (not shown).

The inoculation port 126 may contain at least one aseptic connector or be welded to the assembly through a length of thermoweldable tubing. Additionally and/or alternatively the external assembly 124 may contain at least one aseptic connection (not shown) through which other fluid materials such as buffers, nutrients, acids, bases, or other regulating fluids are added to the bioreactor assembly 120. At least one vent filter assembly 128, which may contain a plurality of sterilizing and/or non-sterilizing grade vent filters, may be connected to the external assembly 124 with a length of tubing or with a plurality of aseptic connectors (not shown).

The bioreactor assembly 120 may contain at least one valve 130, which may be operated by a mechanical, magnetic, pneumatic, and/or hydraulic movement, so that, when the valve 130 is in an open state, the fluid material may be pumped out of the bioreactor assembly 120 chamber using at least one pump 132, which supplies the fluid through at least one length of tubing to the at least one perfusion assembly 134.

The at least one perfusion assembly 134 may be utilized to collect the desired biological components as harvest material from the cell of the bioreactor assembly 120 using at least one separation method. The perfusion assembly 134 allows for continuous processing of the bioreactor assembly 120 with multiple harvests and/or with higher cell densities. The separation method may be a multi-use or single-use method including but not limited to centrifugation, single-use centrifugation, capillary fibers and/or membrane filtration, Hydrocyclones®, tangential flow filtration (crossflow), spinfilters, membrane adsorption, or the use of ultrasonic waves (sonoperfusion).

The perfusion assembly 134 may be connected to the bioreactor assembly 120. As explained, the pump 132 pushes the material from the bioreactor into the perfusion assembly 134 to undergo separation using at least one perfusion separation method in which the harvest material(s) (cells, proteins, antibodies, etc.) are extracted from the bioreactor biological material. A pump 136 and an aseptic connector 138 may be used to send the harvest material(s) for further processing.

The remaining bioreactor material that is not part of the harvest material(s) may be recirculated back into the bioreactor assembly 120 via a pump 140. External feed material to replenish the bioreactor assembly 120 with media, proteins, and essential nutrients may come from the at least one mixing assembly 106 or may be pumped into the bioreactor assembly 120 through the external assembly 124 from an external feed source (not shown).

The harvest line of the perfusion assembly 134 may be opened manually, at a set time, or at a particular cell concentration to allow the harvest material from the bioreactor assembly to undergo further processing. The biological harvest material from the bioreactor assembly 120 may undergo further processing utilizing at least one processing method such as centrifugation, filtration, crossflow filtration, ultrafiltration, membrane adsorption, column chromatography, and/or concentration.

In this example the biological harvest material may undergo processing by centrifugation using the single-use centrifugation assembly 142, filtration using the filtration assembly 146, 148 and 150, and ultrafiltration and concentration utilizing a crossflow assembly 166.

The single-use centrifugation assembly 142 may be utilized for clarification and/or concentration and washing of the harvest material. The single-use centrifugation assembly 142 may comprise a plurality of single-use centrifugal cells (not shown), an internal rotor assembly (not shown), an internal fluid assembly (not shown) to supply fluid material from the bioreactor assembly 120 into the single-use centrifugal cells as well as external fluid for rinsing, fluid lines (not shown) for removing and collecting waste products, and a rigid covering assembly (not shown) to protect the other components within the single-use chamber 100 from the high rotational speed in the interior of the single-use centrifugation assembly 142.

The single-use centrifugation assembly 142 may utilize a single-use centrifugation platform e.g. from kSep® Systems, wherein a plurality of single-use cells are filled with the fluid containing the biological material from the bioreactor assembly 120 and rotated at a high speed using a rotor assembly. The internal rotor assembly (not shown) may connect to a reusable external motor assembly (not shown) may connect to an external motor via one of the connection mechanisms explained above. The connection of the external motor assembly (not shown) to the internal rotor assembly (not shown) may comprise a venting assembly (not shown) including a sterilizing grade membrane filter (not shown) to properly vent the airflow generated by the rotational force from the centrifuge.

The internal fluid assembly (not shown) may comprise a plurality of tubing lines that may supply the single-use centrifugal cells (not-shown) with fluids and remove waste products from the cells. The plurality of tubing lines may be aseptically connected to an external source. The tubing lines (not shown) may be expertly positioned with a rotational joint (not shown) to prevent the tubing lines from becoming tangled during centrifugation.

The rigid covering assembly may be made of a rigid, sterilizable (preferably gamma-irradiatable) plastic material to protect other components internal to the single-use chamber 100. While the single-use centrifugal cells (not-shown), the internal rotor assembly (not shown), the internal fluid assembly (not shown), and the rigid covering assembly (not shown) are discarded, the external motor assembly (not shown) may be reusable.

Depending on where the desired biological harvest material is located after centrifugation, either the dense pelletized material or the supernatant fluid may be collected for further processing. Dense materials may be resuspended in a fluid buffer to provide as a fluid suspension that undergoes further processing. The biological harvest material may be flushed with a series of rinses using buffers and/or concentrated by removing non-essential fluids during processing.

The biological harvest material from the single-use centrifuge assembly 142 may be pumped out using pump 144 for further processing. In this example the biological harvest material is further processed by filtration using at least one filtration assembly. The at least one filtration assembly may comprise a plurality of filters that may be hydrophilic or hydrophobic filters, a depth filter, a pre-filter, a sterilizing grade filter, a *mycoplasma* retentive filter, a cross-flow (tangential flow) filter, an ultrafiltration filter, a membrane adsorption filter, a virus retentive filter or some combination of filters arranged as a filter train assembly.

The at least one filtration assembly in this example consists of at least one depth filter 146, at least one prefilter 148, and at least one sterilizing grade filter 150. In alternative examples at least one membrane adsorber, such as a Sartobind® membrane adsorber with a specific surface chemistry, and/or at least one column for chromatography may be utilized for the capture and/or the capture and elution of a biological material for processing the biological material.

The filtrate of the biological harvest material may be stored in at least one internal container 154. The at least one internal container 154 may be made from a rigid, non-deformable, sterilizable (preferably gamma irradiatable) plastic. The at least one internal container 154 may contain at least one valve 152 that is in the open state during filling of the container and in a closed state during transfer of the material utilizing a pneumatic drive method.

At least one vent filter 155 may vent the at least one internal container 154 during filling with a fluid. At least one pneumatic airline 158 may be connected to the at least one external assembly 156 that enables a fluid connection from the exterior to the interior of the single-use chamber 100. The pneumatic airline 158 may be connected to the vent filter 155 to supply sterile air, which serves as a pressure source to drive the filtrate of the collected biological harvest material through a dip tube 160 within the internal container 154 to undergo further processing. In this example the collected biological harvest material flows up the dip tube 160 into at least one length of tubing, to at least one aseptic connector 162, and to at least one length of tubing 164 connected to a crossflow assembly 166.

The crossflow assembly 166 may further process the biological harvest material through microfiltration, ultra-purification and/or concentration of the fluid volume. After processing from the crossflow assembly 166, the biological harvest material filtrate is collected in at least one internal storage container 170. The at least one internal container 170 may be made from a rigid, non-deformable, sterilizable (preferably gamma irradiatable) plastic. The at least one internal container 170 may contain at least one valve 168 which is in the open state during filling of the container 170 and in a closed state during transfer of the material utilizing a pneumatic drive method.

At least one vent filter 172 may vent the at least one internal container 170 during filling with a fluid. At least one pneumatic airline 174 may be connected to the at least one external assembly 156 that is enables a fluid connection from the exterior to the interior of the single-use chamber 100. The pneumatic airline 174 may be connected to the vent filter 172 to supply sterile air, which serves as a pressure source to drive the filtrate of the collected biological harvest material through a dip tube 176 within the internal container 170 to undergo dispensing in the at least one sterile dispensing assembly 182.

The at least one sterile dispensing assembly 182 may comprise at least one sterile bag dispensing manifold, at least one bottle-filling unit, at least one syringe-filling unit, at least one lyophilization unit, at least one capsule-filling unit, and/or other sterile dispensing device. In this example the collected biological harvest material flows up the dip tube 176 into at least one length of tubing, to at least one aseptic connector 178, and to at least one length of tubing 180 connected to the at least one sterile dispensing assembly 182.

The at least one sterile dispensing assembly 182 is a sterile bag that serves as dispensing manifold and may fill a plurality of sterilized bags 186 with the processed and purified biological harvest material. The internal sterile bag may be fluidly connected to the plurality of sterilized bags 186 external to the single-use chamber 100 through a plurality of ports 184, wherein the tubing from the plurality of sterilized bags 186 may be aseptically connected to the sterile dispensing assembly 182. The purified biological harvest material may collectively fill the plurality of sterilized bags 186 or serially fill the plurality of sterilized bags 186 through a series of valves (not shown) within the sterile bag. Additionally, the plurality of sterile bags may be filled on a weighing platform (not shown) such as the FlexAct® MF Manifold Filling platform (not shown), where a precise volume and weight of material may be uniformly filled into the plurality of sterile bags 186. As an individual sterile bag is being filled with the purified biological harvest material on at least one weighing platform (not shown), at least one valve (not shown) may divert the flow of the material into another sterile bag (not shown) after reaching a specified weight range.

The plurality of sterilized bags 186 may contain at least one vent filter 188 to assist with filling of the bag. Tubing clips 190 may be available on the length of tubing that joins the ports 184 to the sterilized bags 186 to clamp off the flow of fluid material into the sterile bags 186. The tubing clips 190 may be manually and/or automatically closed using a sealing device. The filled sterilized bags 186 may be aseptically disconnected from the assembly using an aseptic disconnection device, e.g. by heat sealing a thermoplastic tubing such as with the Biosealer®, by using radio frequency sealing with a Sebra® RF sealing tool, by using external clips and a blade to cut a length of tubing such as with the Clipster®, by using an external collar around the tubing such as with a Quickseal®, or other aseptic disconnection device.

The purified biological harvest material may be an intermediate material requiring further processing and/or a final product material which may be utilized in a medical treatment. The plurality of sterilized bags 186 filled with purified biological harvest material may undergo uniform freezing for long-term storage, e.g. using a Celsius® freezing device.

Figure 3:
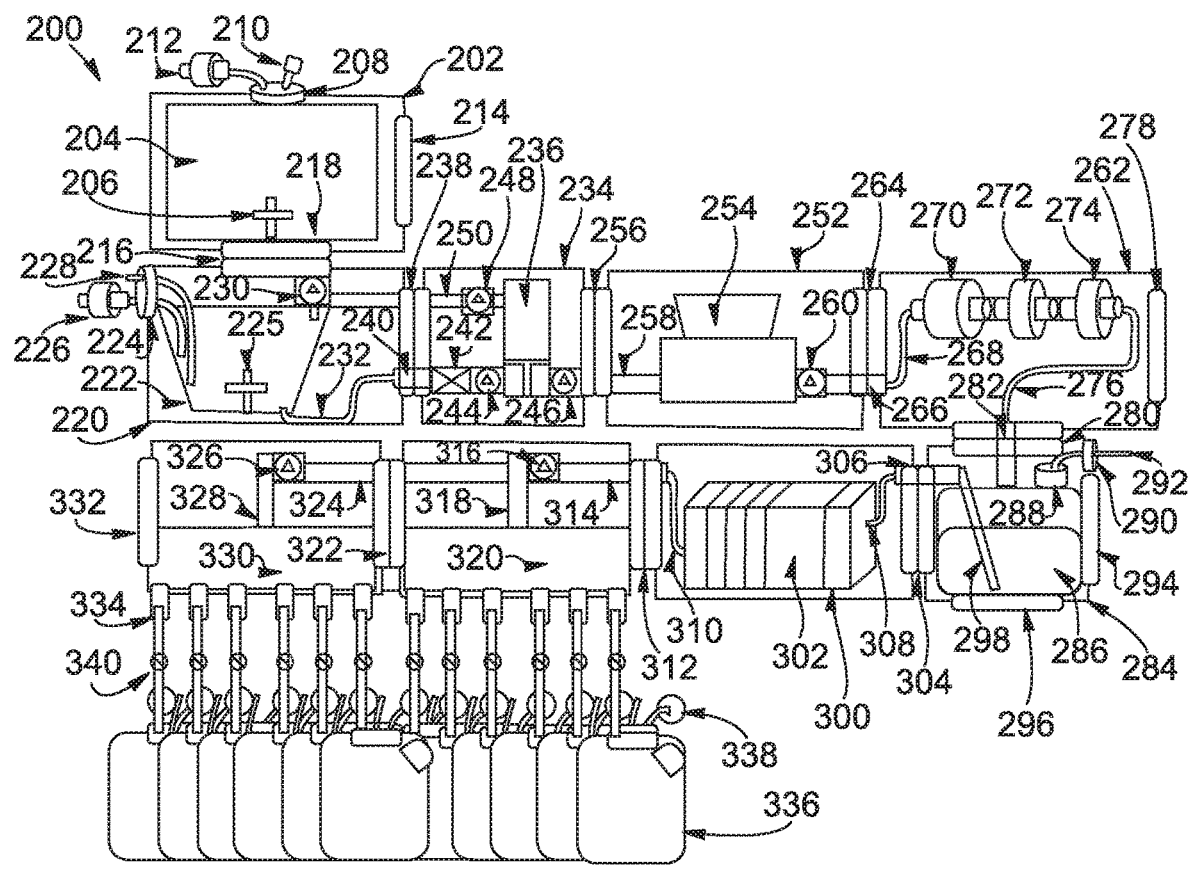
FIG. 3 illustrates an example of a manufacturing system for the upstream and downstream processing of a biological material within a network of single-use containers.

FIG. 3 illustrates an example of a manufacturing system for the upstream and downstream processing of a biological material within a network of single-use containers 200.

The manufacturing system of FIG. 3 is similar to the one of FIG. 2, the only difference being that the different assemblies are contained in different single-use chambers connected to each other to form a network 200.

The network of single-use chambers 200 comprises individualized single-use chambers, i.e. each chamber has its own specific functionality that contributes to the processing of a biological material inside the network of single-use chambers 200. The network of single-use chambers 200 provides a flexible, configurable, sterile platform for the manufacture of biological materials.

Each of the single-use chambers may comprise one or more flexible walls made from a single-use film material, one or more rigid walls made from plastic, or a combination of at least one flexible wall and at least one rigid wall. At least one of the chambers within the network of single-use chambers 200 may be thermally regulated by at least one external assembly (not shown).

In this example the network of single-use chambers 200 includes but is not limited to at least one of the following chambers: a mixing assembly chamber 202, a bioreactor assembly chamber 220, a perfusion assembly chamber 234, a centrifugation assembly chamber 252, a filtration assembly chamber 262, a fluid storage assembly chamber 284, a crossflow purification and concentration assembly chamber 300, a filling assembly chamber 320, and an additional filling assembly chamber 330.

All of the components and assemblies of the single-use chamber network 200 may be sterilized using an approved sterilization method such as by gamma-irradiation, autoclaving, steam-in-place, or chemical sterilant (such as ethylene oxide or vaporized hydrogen peroxide). In this example the network of single-use chambers 200 contain flexible, film walls which have undergone sterilization by gamma irradiation. Components that cannot undergo sterilization by the method selected for the network of single-use chambers 200 may be sterilized using an alternative sterilization method and aseptically connected to the network of single-use chambers 200 and/or the individual chambers post-sterilization.

Each of the individualized chambers within the network of single-use chambers 200 may be vented using at least one vent filter assembly (not shown), which may contain a plurality of sterilizing and/or non-sterilizing grade vent filters. The at least one vent filter assembly (not shown)

maintains a sterilized air space within the individual chambers and/or within the network of single-use chambers 200. Any sterilizing grade filters of the at least one vent filter assembly (not shown) may be integrity testable to ensure sterility within the individual chambers and/or within the network of single-use chambers 200.

Each of the individualized chambers may be aseptically connected to one another to form a network of single-use chambers 200 using at least one transfer hatch assembly 214, 216, 238, 256, 264, 278, 280, 294, 296, 304, 312, 322 and 332, which may be utilized to add and/or remove components, units, consumables, and/or final products into or out of the network of single-use chambers 200. The at least one transfer hatch assembly 214, 216, 238, 256, 264, 278, 280, 294, 296, 304, 312, 322, & 332 may be aseptically connected to a sterile transfer bag for aseptically moving products out from the network of single-use chambers 200. Additionally or alternatively a glove assembly (not shown) may be aseptically connected to the at least one transfer hatch assembly 214, 216, 238, 256, 264, 278, 280, 294, 296, 304, 312, 322 and 332 for troubleshooting, moving stuck components internal to the individual chambers and/or the network of single-use chambers 200 during processing, and/or for manually moving internal components around.

The at least one mixing assembly chamber 202 may be utilized to mix media, nutrient rich broths, and buffers to support the growth of at least one biological material in the at least one bioreactor chamber assembly 220. The mixing assembly chamber 202 may contain at least one internal envelope 204 that holds the fluid volume for mixing. The envelope 204 may additionally or alternatively be a container inside the mixing assembly chamber. The mixing assembly in the mixing assembly chamber 202 may have the same features and function in the same way as the mixing assembly 106 described with reference to FIG. 2. In particular, the mixing device such as an impeller 206, the at least one external assembly 208, the at least one filter assembly 212 and the at least one vent filter assembly 210 correspond to the elements with the same name in the mixing assembly 106.

All other individualized chambers within the network of single-use chambers 200 may contain similar external assembly 208, filter assembly 212, aseptic connection (not shown), and/or vent filter assembly.

The mixing assembly chamber 202 may contain a plurality of transfer hatch assemblies to connect to other individualized chambers to form a network of single-use chambers 200. In this example the mixing assembly chamber 202 contains a transfer hatch assembly 216 that aseptically connects to the at least one bioreactor chamber assembly 220. The aseptic connection may include a fluid connection to the internal part of the mixing assembly chamber 202, in particular the at least one envelope 204, and/or a fluid line from the at least one envelope 204.

In this example the mixing assembly chamber 202 contains an additional transfer hatch 214, in case an additional mixing chamber (not shown) or another individualized chamber needs to be connected to the network of single-use chambers 200 for the purposes of processing a biological material. The least one cell and/or envelope 204 may contain at least one valve (not shown) so that, when the valve is in an open state the fluid material may be pumped out of the internal envelope 204 from the mixing assembly chamber 202 to the at least one bioreactor assembly chamber 220 through at least one length of tubing 218.

The at least one length of tubing 218 may be aseptically connected to form a fluid connection between the at least one internal envelope 204 and an internal envelope 222 internal to the at least one bioreactor assembly chamber 220 using the transfer hatch assembly 216, which also forms an aseptic connection with the tubing line 218. The at least one length of tubing 218 may use at least one pump 230, which in this example is residing in the at least one bioreactor assembly chamber 220, to pump fluid from the at least one internal envelope 204 of the at least one mixing assembly chamber 202 into the envelope 222 internal to the at least one bioreactor assembly chamber 220. The at least one pump 230 may connect to an external motor via one of the connection mechanisms explained above.

The at least one bioreactor assembly chamber 220 may contain at least one internal bioreactor envelope 222. The bioreactor assembly in the bioreactor assembly chamber 220 may have the same features and function in the same way as the bioreactor assembly 120 described with reference to FIG. 2. In particular, the mixing device such as an impeller 225, the at least one external assembly 224, the at least one inoculation port 228 and the at least one vent filter assembly 226 correspond to the elements with the same name in the bioreactor assembly 120.

The internal envelope 222 may contain at least one valve (not shown), which may be operated by a mechanical, magnetic, pneumatic, and/or hydraulic movement. When the valve is in an open state, the biological fluid material may be pumped out of the internal envelope 222 through at least one length of tubing 232. In this example the at least one bioreactor assembly chamber 220 contains at least one transfer hatch assembly 238 that aseptically connects to the at least one perfusion assembly chamber 234. The aseptic connection may include a fluid connection to the internal part of the at least one bioreactor assembly chamber 220, in particular the internal envelope 222, and/or at least one length of tubing 232 from the internal envelope 222.

The at least one length of tubing 232 may be aseptically connected to form a fluid connection between the at least one envelope 222 and the at least one perfusion assembly chamber 234 using the transfer hatch assembly 238, which also forms at least one aseptic connection 240 with the tubing line 232. The at least one aseptic connection 240 may use at least one valve 242, which allows biological fluid material generated from the at least one bioreactor assembly chamber 220 into the perfusion assembly 236. The valve 242 may be operated by a mechanical, magnetic, pneumatic, and/or hydraulic movement, so that, when it is in an open state, the biological fluid material may be pumped in the perfusion assembly 236 using a pump 244.

The pump 244, which in this example is residing in the at least one perfusion assembly chamber 234, is used to pump fluid from the at least one internal bioreactor envelope 222 into the perfusion assembly 236. The at least one perfusion assembly chamber 234 may be utilized to collect the desired biological components as harvest material from the bioreactor assembly chamber 220 using at least one separation method.

The perfusion assembly 236 in the perfusion assembly chamber 234 may have the same features and function in the same way as the perfusion assembly 134 described with reference to FIG. 2.

A pump 246 and at least one length of tubing 258 aseptically connected through the transfer hatch assembly 256 are used to fluidly connect the perfusion assembly chamber 234 with the centrifugation assembly chamber 252 to send the fluid biological harvest material for further processing. The remaining fluid bioreactor material that is not part of the harvest material may be recirculated back into the internal envelope 222 via a pump 248 and a length of tubing 250 that is aseptically connected with the bioreactor assembly chamber 220 through transfer hatch assembly 238.

The fluid biological harvest material from the bioreactor assembly chamber 220 may undergo further processing utilizing at least one processing method such as centrifugation, filtration, crossflow filtration, ultrafiltration, membrane adsorption, column chromatography, and/or concentration. In this example the biological harvest material undergoes processing by centrifugation using a single-use centrifugation assembly chamber 252, filtration using a filtration assembly chamber 262, and ultrafiltration and concentration utilizing a crossflow assembly chamber 300.

The single-use centrifugation assembly 254 within the centrifugation assembly chamber 252 may have the same features and function in the same way as the single-use centrifugation assembly 142 described with reference to FIG. 2.

The fluid biological harvest material from the single-use centrifuge assembly 254 may be pumped out using a pump 260 for further processing. In this example the at least one centrifugation assembly chamber 252 contains at least one transfer hatch assembly 264 which aseptically connects to the at least one filtration assembly chamber 262. The aseptic connection may include a fluid connection between the centrifugation assembly 254 and the at least one filtration assembly chamber 262, e.g. at least one length of tubing 266.

In this example the fluid biological harvest material is further processed by filtration using at least one filtration assembly 262 where at least one length of tubing 268 connects to the filter train. The at least one filtration assembly 262 may contain a plurality of filters which may be hydrophilic or hydrophobic filters, a depth filter, a pre-filter, a sterilizing grade filter, a *mycoplasma* retentive filter, a cross-flow (tangential flow) filter, an ultrafiltration filter, a membrane adsorption filter, a virus retentive filter or some combination of filters arranged as a filter train assembly. The at least one filtration assembly 262 in this example comprise at least one depth filter 270, at least one prefilter 272, and at least one sterilizing grade filter 274.

In this example the at least one filtration assembly chamber 262 contains at least one transfer hatch assembly 280 that aseptically connects to at least one fluid storage assembly chamber 284. The aseptic connection may include a fluid connection from the filtration assembly chamber 262 to the at least one fluid storage assembly chamber 284, e.g. at least one length of tubing 276. In this example the filtration assembly chamber 262 contains an additional transfer hatch 278 in case an additional filtration assembly chamber (not shown) or another individualized chamber needs to be connected to the network of single-use chambers 200 for the purposes of processing a biological material.

The filtrate of the biological harvest material may be stored in at least one fluid storage assembly chamber 284 that comprises at least one internal container 286. The at least one internal container 286 may have the same features and function in the same way as the internal container 154 described with reference to FIG. 2. In particular, the at least one vent filter 288, the at least one pneumatic airline 292, the at least one external assembly 290 and the dip tube 298 correspond to the elements with the same name relating to the internal container 154 of FIG. 2.

In this example the collected biological harvest material flows up the dip tube 298 into at least one length of tubing, to at least one aseptic connector 306, which is connected to the at least one crossflow purification and concentration assembly chamber 300 through the at least one transfer hatch assembly 304. In this example the fluid storage assembly chamber 284 contains additional transfer hatches 294 and 296 to allow the container to serve as a connection hub within the network of single-use chambers 200. Additional individualized chambers (not shown) may be connected to the network of single-use chambers 200 through the transfer hatches 294 and 296 on the fluid storage assembly chamber 284 for the purposes of processing a biological material as required.

The at least one crossflow purification and concentration assembly chamber 300 contains at least one crossflow assembly 302 that may further process the biological harvest material through microfiltration, ultra-purification and/or concentration of the fluid volume. The crossflow assembly 302 is fluidly connected by at least one length of tubing 308 to aseptic connector 306 to receive the filtrate of the biological harvest material, which is pressure-controlled by the pneumatic pressure line 292.

After processing from the crossflow assembly 302 the biological harvest material filtrate moves through at least one length of tubing 310 into the at least one filling assembly chamber 320. In this example the at least one crossflow purification and concentration assembly chamber 300 contains the at least one transfer hatch assembly 312 that aseptically connects to the at least one sterile dispensing assembly chamber 320. In alternative examples the at least one crossflow purification and concentration assembly chamber 300 may be aseptically connected with transfer hatch assembly 312 to an additional fluid storage assembly chamber (not shown). The aseptic connection may include a fluid connection from the crossflow purification and concentration assembly chamber 300 to the at least one sterile dispensing assembly chamber 320, e.g. at least one length of tubing 310 and/or at least one aseptic connector 314.

The at least one sterile dispensing assembly chamber 320 may comprise at least one sterile bag dispensing manifold, at least one bottle-filling unit, at least one syringe-filling unit, at least one lyophilization unit, at least one capsule-filling unit, and/or other sterile dispensing device. In this example the biological harvest material is pumped from the crossflow purification and concentration assembly chamber 300 into the at least one length of tubing 310, to at least one aseptic connector 314, through pump 316, into at least one sterile bag dispensing manifold 318.

The at least one sterile dispensing assembly chamber 320 contains at least one sterile bag dispensing manifold 318 that may fill a plurality of sterilized bags 336 with the processed and purified biological harvest material. The internal sterile bag dispensing manifold 318 may be fluidly connected to the plurality of sterilized bags 336 external to the network of sterilized chambers 200 through a plurality of ports 334, wherein the tubing from the plurality of sterilized bags 336 may be aseptically connected to the sterile dispensing assembly chamber 320. The purified biological harvest material may collectively fill the plurality of sterilized bags 336 or serially fill the plurality of sterilized bags 336 through a series of valves (not shown) within the sterile bag dispensing manifold 318.

Additional sterile dispensing assembly chambers, which in this example include sterile dispensing assembly chamber 330, may be aseptically attached to the sterile dispensing assembly chamber 320 through the transfer hatch 322. The aseptic connection may include a fluid connection from the sterile dispensing assembly chamber 320 to the other sterile dispensing assembly chamber 330, e.g. at least one aseptic connector 324. In this example the biological harvest material is pumped from the crossflow purification and concentration assembly chamber 300 through the sterile dispensing assembly chamber 320 and into the additional sterile dispensing assembly chamber 330.

The fluid connection with the sterile bag dispensing manifold inside the sterile dispensing assembly chamber 320 may be closed off with a valve (not shown) after the plurality of sterilized bags 336 are completely filled, thus requiring additional sterilized bags 336. The fluid would then be diverted through the at least one aseptic connector 314, through pump 316, into the at least one aseptic connector 324, through pump 326, into at least one sterile dispensing bag dispensing manifold 328. The plurality of sterilized bags 336 may contain at least one vent filter 338 to assist with filling of the bag chamber. Tubing clips 340 may be available on the length of tubing that joins the ports 334 to the sterilized bags 336 to clamp off the flow of fluid material into the sterile bags 336. The tubing clips 340 may be manually and/or automatically closed using a sealing device. The filled sterilized bags 336 may be aseptically disconnected from the assembly using an aseptic disconnection device such as those described with reference to FIG. 2. The purified biological harvest material may be an intermediate material requiring further processing and/or a final product material that may be utilized in a medical treatment. The plurality of sterilized bags 336 filled with purified biological harvest material may undergo uniform freezing for long-term storage, e.g. using a Celsius® freezing device.

Figure 4:
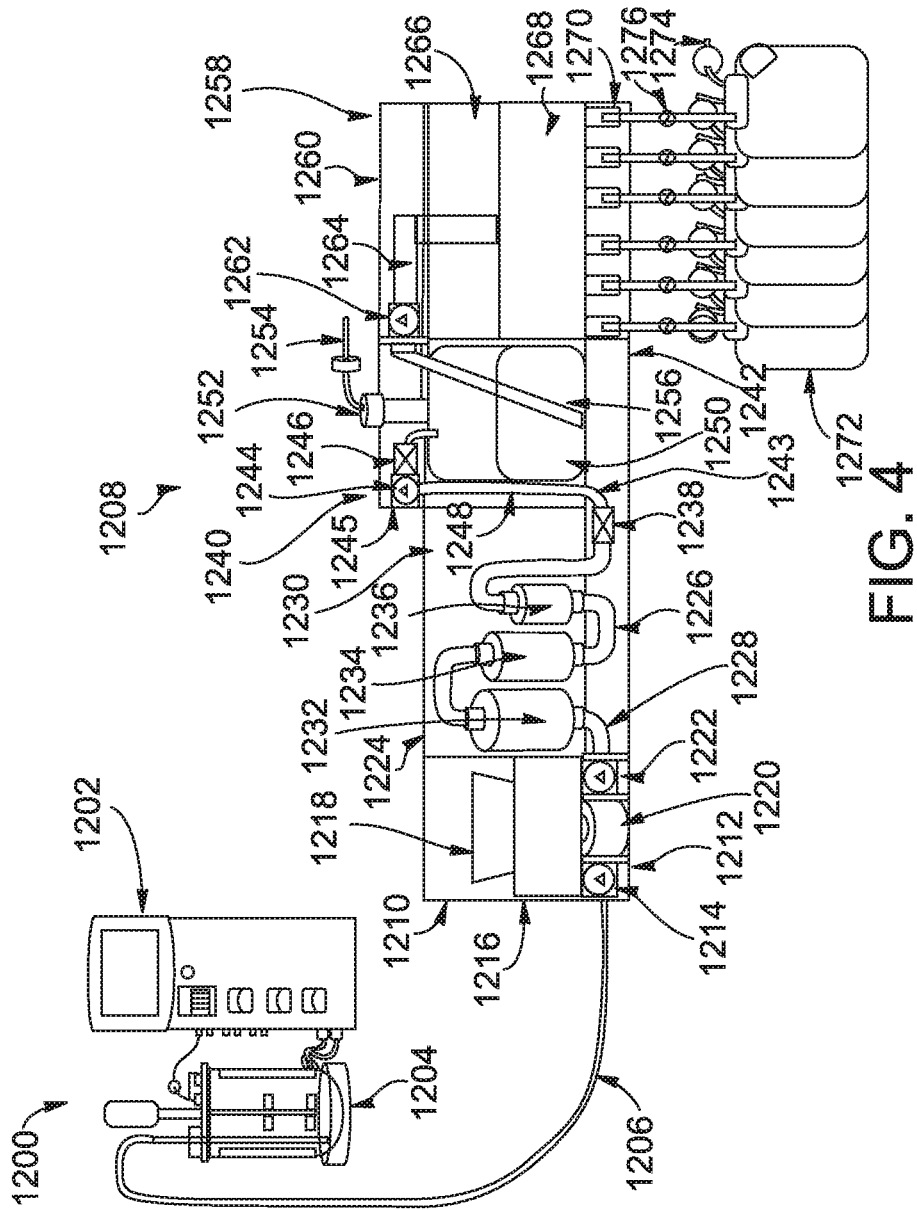
FIG. 4 illustrates an example of a manufacturing system for the upstream and downstream processing of a biological material within a network of single-use containers utilizing a single-use bioreactor for production of the source biological material.

FIG. 4 illustrates an example of a manufacturing system for the upstream and downstream processing of a biological material within a network of single-use containers utilizing a single-use bioreactor for production of the source biological material.

This example shows a benchtop manufacturing setup 1200 that may include at least one bioreactor control unit 1202, at least one single-use bioreactor 1204 and at least one network of single-use chambers 1208, which may comprise one or more flexible walls made from a single-use film material, one or more rigid walls made from plastic, or a combination of at least one flexible wall and at least one rigid wall. The network of single-use chambers 1208 comprises individualized single-use chambers, each with its own functionality required for the processing of a biological material internally to the network.

In this example the network of single-use chambers 1208 includes but is not limited to at least one of the following chambers: a centrifugation assembly chamber 1210, a filtration assembly chamber 1224, a fluid storage assembly chamber 1240, and a dispensing assembly chamber 1258 for the sterile filling of single-use bags 1272. All or some of the components and assemblies of the network of single-use chambers 1208 may be sterilized using an approved sterilization method.

Each of the individualized chambers within the network of single-use chambers 1208 may be vented using at least one vent filter assembly (not shown), which may comprise a plurality of sterilizing and/or non-sterilizing grade vent filters. The at least one vent filter assembly (not shown) maintains a sterilized air space within the individual chambers and/or within the network of single-use chambers 1208. Any sterilizing grade filters from the at least one vent filter assembly (not shown) may be integrity testable to ensure sterility within the individual chambers and/or within the network of single-use chambers 1208. Each of the individualized chambers may be aseptically connected to one another to form a network of single-use chambers 1208 as described with reference to FIG. 1.

The at least one bioreactor control unit 1202 controls at least one single-use bioreactor 1204, which may be a benchtop bioreactor or a large-scale good-manufacturing-practice (GMP) production bioreactor. In alternative examples a multi-use stainless steel, plastic, or perfusion bioreactor may be utilized. At least one mixing assembly (not shown) may be aseptically connected to the at least one single-use bioreactor 1204 to supply mixed media, nutrient rich broths, and buffers to support the growth of at least one biological material in the at least one single-use bioreactor 1204. At least one length of tubing 1206 may be aseptically connected to and supply the network of single-use chambers 1208 with the biological fluid material from the at least one single-use bioreactor 1204.

In this example the network of single-use chambers 1208 initiates with a centrifugation assembly chamber 1210 comprising a primary subchamber 1216 and a secondary subchamber 1212. The centrifugation assembly chamber 1210 may utilize a single-use centrifugation platform e.g. from kSep® Systems, wherein a plurality of single-use chambers are filled with the fluid containing the biological material from the single-use bioreactor assembly 1204 and rotated at a high speed using a rotor assembly as previously described. The fluid biological material enters into the secondary subchamber 1212, where a metered volume of fluid is pumped into the centrifugation assembly 1218 via pump 1214.

In this example a centrifugation assembly 1218 is located within the primary subchamber 1216. The centrifugation assembly 1218 may contain a rigid covering assembly, which may be made of a rigid, sterilizable (preferably gamma-irradiatable) plastic material to protect other components internal to the centrifugation assembly 1218. While the single-use centrifugal chambers (not-shown), the internal rotor assembly (not shown), the internal fluid assembly (not shown), and the rigid covering assembly (not shown) are discarded, the external motor assembly (not shown) may be reusable.

The centrifugation motor assembly 1220 is within the secondary subchamber 1212. The centrifugation motor assembly 1220 may connect to a reusable external motor assembly (not shown) with a direct connection containing sealed bearings, an extension of the motor shaft into an envelope of the shaft in the centrifugation assembly 1218, a magnetic coupling, a superconducting magnetic coupling, and/or a fluid drive connection. The connection of the external motor assembly (not shown) to the internal rotor assembly (not shown) may contain a venting assembly (not shown) comprising a sterilizing grade membrane filter (not shown) to properly vent the airflow generated by the rotational force from the centrifuge. Depending on where the desired fluid biological harvest material is located after centrifugation, either the dense pelletized material or the supernatant fluid may be collected for further processing. Dense materials may be resuspended in a fluid buffer to provide as a fluid suspension to undergo further processing. The fluid biological harvest material may be flushed with a series of rinses using buffers and/or concentrated by removing non-essential fluid during processing. The fluid biological harvest material from the centrifuge assembly 1218 may be pumped out using a pump 1222 for further processing.

In this example the centrifugation assembly chamber 1210 connects to the at least one filtration assembly chamber 1224 comprising a primary subchamber 1230 and a secondary subchamber 1226. The centrifugation assembly chamber 1210 connects to the at least one filtration assembly chamber 1224 through the aseptic connection of the secondary subchambers 1212 and 1226 as previously described.

In this example the fluid biological harvest material is further processed by filtration using at least one filtration assembly chamber 1224 where at least one length of tubing 1228 connects to the filter train. The at least one filtration assembly chamber 1224 may contain a plurality of filters within the primary subchamber 1230, which may comprise hydrophilic or hydrophobic filters, a depth filter, a pre-filter, a sterilizing grade filter, a *mycoplasma* retentive filter, a cross-flow (tangential flow) filter, an ultrafiltration filter, a membrane adsorption filter, a virus retentive filter or some combination of filters arranged as a filter train assembly.

The at least one filtration assembly chamber 1224 in this example comprises at least one depth filter 1232, at least one prefilter 1234, and at least one sterilizing grade filter 1236. The filtration assembly chamber 1224 may contain at least one valve 1238 in the secondary subchamber 1226, so that, when the valve 1238 is in an open state, the filtrate of the biological fluid material may be pumped out through at least one length of tubing.

In this example the filtration assembly chamber 1224 connects to the at least one fluid storage assembly chamber 1240, which comprises a primary subchamber 1248, a secondary subchamber 1242 and a tertiary subchamber 1245, through the aseptic connection of the secondary subchambers 1226 and 1242 as previously described. The filtrate of the biological harvest material may be stored in the at least one fluid storage assembly chamber 1240, which contains within the primary subchamber 1248 at least one internal container 1250, which may be made from a rigid, non-deformable, sterilizable (preferably gamma irradiatable) plastic. The filtrate of the biological harvest material may be pumped through a length of tubing 1243 via a pump 1244.

The at least one internal container 1250 may contain at least one valve 1246 that is in an open state during filling and in a closed state during transfer of the material utilizing a pneumatic drive method. At least one external assembly 1252 containing at least one vent filter may vent the at least one internal container 1250 during filling with a fluid. At least one pneumatic airline 1254 may be connected to the at least one external assembly 1252 that enables a fluid connection from the exterior to the interior of the single-use chamber 1240. The pneumatic airline 1254 may supply a sterile air pressure source to drive the filtrate of the collected biological harvest material through the dip tube 1256 within the internal container 1250 to undergo further processing.

In this example the collected biological harvest material flows up the dip tube 1256 into at least one length of tubing and then into at least one sterile dispensing assembly chamber 1258 comprising at least one sterile bag dispensing manifold 1268 that may fill a plurality of sterilized bags 1272 with the processed and purified biological harvest material. The at least one sterile dispensing assembly chamber 1258 comprises a primary subchamber 1266, a secondary subchamber 1270 and a third subchamber 1280. The at least one fluid storage assembly chamber 1240 connects to the at least one sterile filling assembly chamber 1258 through the aseptic connection of the secondary subchambers 1242 and 1270 and tertiary subchambers 1245 and 1260 as previously described.

The internal sterile bag dispensing manifold 1268 within the primary subchamber 1266 may be fluidly connected to the plurality of sterilized bags 1272 external to the network of sterilized chambers through a plurality of ports, wherein the tubing from the plurality of sterilized bags 1272 may be aseptically connected to the internal sterile bag dispensing manifold 1268. The purified biological harvest material may collectively fill the plurality of sterilized bags 1272 or serially fill the plurality of sterilized bags 1272 through a series of valves (not shown) within the sterile bag dispensing manifold 1268. Additional sterile dispensing assembly chambers (not shown) may be aseptically attached to the sterile dispensing assembly chamber 1258.

The aseptic connection from the fluid dip tube 1256 into the tertiary subchamber 1260 may include at least one pump 1262 and at least one fluid piping connection 1264 to the internal sterile bag dispensing manifold 1268. The plurality of sterilized bags 1272 may contain at least one vent filter 1274 to assist with filling of the bags. Tubing clips 1276 may be available on the length of tubing that joins the ports to the sterilized bags 1272 to clamp off the flow of fluid material into the sterile bags 1272. The tubing clips 1276 may be manually and/or automatically closed using a sealing device. The filled sterilized bags 1272 may be aseptically disconnected from the assembly using an aseptic disconnection device such as those described with reference to FIG. 2. The purified biological harvest material may be an intermediate material requiring further processing and/or a final product material which may be utilized in a medical treatment. The plurality of sterilized bags 1272 filled with purified biological harvest material may undergo uniform freezing for long-term storage, e.g. using a Celsius® freezing device.

Figure 5:
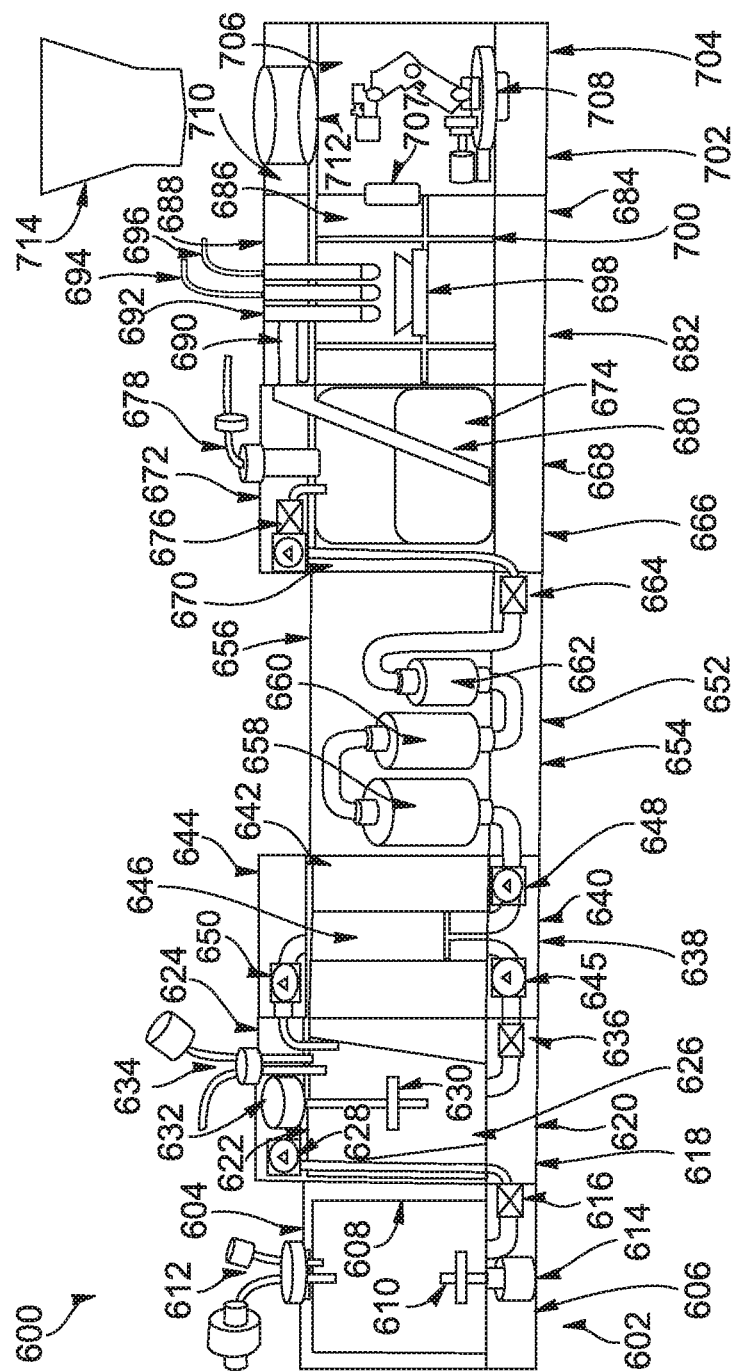
FIG. 5 illustrates an example of a manufacturing system for the upstream and downstream processing of a biological material within a network of single-use containers for three-dimensional printing of a biological product.

FIG. 5 illustrates an example of a manufacturing system for the upstream and downstream processing of a biological material within a network of single-use containers for three-dimensional printing of a biological product.

This example shows a network of single-use chambers 600 that may comprise one or more flexible walls made from a single-use film material, one or more rigid walls made from plastic, or a combination of at least one flexible wall and at least one rigid wall. The network of single-use chambers 600 comprises individualized single-use chambers, each with its own functionality required for the processing of a biological material internally to the network.

In this example the network of single-use chambers 600 includes but is not limited to at least one of the following chambers: a mixing assembly chamber 602, a bioreactor assembly chamber 618, a perfusion assembly chamber 638, a filtration assembly chamber 652, a fluid storage assembly chamber 666, a 3-dimensional printing chamber 682, a robotic manipulation chamber 702, and a transfer hatch 712 for the sterile removal of the 3D printed biological product. All or some of the components and assemblies of the single-use chambers 600 may be sterilized using an approved sterilization method.

Each of the individualized chambers within the network of single-use chambers 600 may be vented using at least one vent filter assembly (not shown), which may comprise a plurality of sterilizing and/or non-sterilizing grade vent filters. The at least one vent filter assembly (not shown) maintains a sterilized air space within the individual chambers and/or within the network of single-use chambers 600. Any sterilizing grade filters from the at least one vent filter assembly (not shown) may be integrity testable to ensure sterility within the individual chambers and/or within the network of single-use chambers 600. Each of the individualized chambers may be aseptically connected to one another to form a network of single-use chambers 600 as previously described.

The at least one mixing assembly chamber 602 may be utilized to mix media, nutrient rich broths, and buffers to support the growth of at least one biological material in the at least one bioreactor chamber assembly 618. The mixing assembly chamber 602 may contain at least one internal envelope 608 within a primary subchamber 604, wherein the envelope 608 holds the fluid volume for mixing. The mixing assembly chamber 602 may comprise at least one mixing device within the at least one envelope 608, such as an impeller 610 that may connect to at least one motor assembly 614 within a secondary subchamber 606. The mixing shaft assembly with the at least one impeller 610 may comprise a plurality of impeller shapes and designs. The mixing assembly chamber 602 may comprise at least one external assembly 612 for the input of sterile material and/or the sterile venting of the at least one internal envelope 608. All other individualized chambers within the network of single-use chambers 600 may contain a similar external assembly 612.

In this example the mixing assembly chamber 602 connects to the at least one bioreactor chamber assembly 618, which comprises a primary subchamber 622, a secondary subchamber 620 and a tertiary subchamber 624, through the aseptic connection of the secondary subchambers 606 and 620 as previously described. The aseptic connection may include a fluid connection to the internal part of the mixing assembly chamber 602, in particular the at least one envelope 608, and/or a fluid line from the at least one envelope 608.

The mixing assembly chamber 602 may contain at least one valve 616, so that, when the valve 616 is in an open state, the fluid material may be pumped out of the internal envelope 608 from the mixing assembly chamber 602 to the at least one bioreactor assembly chamber 618 through at least one length of tubing. The at least one length of tubing may use at least one pump 628, which in this example is residing in the tertiary subchamber 624 of the at least one bioreactor assembly chamber 618, to pump fluid from the at least one internal envelope 608 of the at least one mixing assembly chamber 602 into an internal bioreactor envelope 626 internal to the primary subchamber 622 of the at least one bioreactor assembly chamber 618.

The at least one internal bioreactor envelope 626 may comprise at least one mixing device, such as an impeller 630, which may connect to at least one motor assembly 632 within the tertiary subchamber 624. The at least one bioreactor assembly chamber 618 may contain an internal and/or external heating element (not shown) that may provide thermal regulation of the bioreactor for optimal cell growth. The heating element (not shown) may utilize recirculation of a heated fluid, an electric heater jacket, a heated coil, and/or forced hot air in the region of the bioreactor assembly chamber 618. At least one of the chambers within the network of single-use chambers 600 may be thermally regulated by at least one external assembly (not shown).

The bioreactor assembly chamber 618 may comprise at least one external assembly 634 for the inoculation of material and/or for the venting the internal bioreactor envelope 626. The internal bioreactor envelope 626 may comprise at least one valve 636, such that, when the valve 636 is in an open state, the biological fluid material may be pumped out through at least one length of tubing.

In this example the bioreactor assembly chamber 618 connects to the at least one perfusion assembly chamber 638, which comprises a primary subchamber 642, a secondary subchamber 640 and a tertiary subchamber 644, through the aseptic connection of the secondary subchambers 620 and 640 as well as the tertiary subchambers 624 and 644 as previously described.

A pump 645, which in this example is residing in the secondary subchamber 640 of the at least one perfusion assembly chamber 638, is used to pump fluid from the at least one internal bioreactor envelope 626 into the perfusion assembly 646 within the primary subchamber 642 of the perfusion assembly chamber 638. The at least one perfusion assembly chamber 638 may be utilized to collect the desired biological components as harvest material from the bioreactor assembly chamber 618 using at least one separation method. The pump 645 moves the fluid material from the bioreactor into the perfusion assembly 646 to undergo separation using at least one perfusion separation method where the harvest material is extracted. Further, a pump 648 and at least one length of tubing are used to connect the perfusion assembly chamber 638 to the filtration assembly chamber 652 for further processing.

The remaining fluid bioreactor material that is not part of the harvest material may be recirculated back into the internal bioreactor envelope 626 via a pump 650 and a length of tubing which is aseptically connected with the bioreactor assembly chamber 618 through tertiary subchambers 624 and 644. External feed material to replenish the internal bioreactor envelope 626 with media, proteins, and essential nutrients may come from the at least one mixing assembly chamber 602 or may be pumped into the internal bioreactor envelope 626. The harvest line of the perfusion assembly 646 may be opened manually, at a set time, or at a particular cell concentration to allow the fluid biological harvest material from the bioreactor assembly chamber 618 to undergo further processing.

In this example the perfusion assembly chamber 638 connects to the at least one filtration assembly chamber 652, which comprises a primary subchamber 656 and a secondary subchamber 654, through the aseptic connection of the secondary subchambers 640 and 654 as previously described. The fluid biological harvest material is further processed by filtration using the at least one filtration assembly chamber 652, wherein at least one length of tubing connects to the filter train. The at least one filtration assembly chamber 652 may comprise a plurality of filters within the primary subchamber 656, which may include hydrophilic or hydrophobic filters, a depth filter, a pre-filter, a sterilizing grade filter, a *mycoplasma* retentive filter, a cross-flow (tangential flow) filter, an ultrafiltration filter, a membrane adsorption filter, a virus retentive filter or some combination of filters arranged as a filter train assembly.

The at least one filtration assembly chamber 652 in this example comprises at least one depth filter 658, at least one prefilter 660, and at least one sterilizing grade filter 662. The filtration assembly chamber 652 may contain at least one valve 664 in the secondary subchamber 654, such that, when the valve 664 is in an open state, the filtrate of the biological fluid material may be pumped out through at least one length of tubing.

In this example the filtration assembly chamber 652 connects to the at least one fluid storage assembly chamber 666, which comprises a primary subchamber 670 and a secondary subchamber 668, through the aseptic connection of the secondary subchambers 652 and 668 as previously described. The filtrate of the biological harvest material may be stored in the at least one fluid storage assembly chamber 666 that contains within the primary subchamber 670 at least one internal container 674, which may be made from a rigid, non-deformable, sterilizable (preferably gamma irradiatable) plastic. The at least one internal container 674 may comprise at least one valve 676 that is in an open state during filling and in a closed state during transfer of the material utilizing a pneumatic drive method. At least one external assembly 678 containing at least one vent filter may vent the at least one internal container 674 during filling with a fluid. At least one pneumatic airline may be connected to the at least one external assembly 678 that enables a fluid connection from the exterior to the interior of the single-use chamber 652, in particular to the interior container 674. The pneumatic airline may supply a sterile air pressure source to drive the filtrate of the collected biological harvest material through the dip tube 680 within the internal container 674 to undergo further processing.

In this example the collected biological harvest material flows up the dip tube 680 into at least one length of tubing into a 3-dimensional printer head supply line 690 in a tertiary subchamber 688 of the at least one 3-dimensional printing assembly chamber 682. The 3-dimensional printing assembly chamber 682 may further comprise a primary subchamber 686 and a secondary subchamber 684. The at least one fluid storage assembly chamber 666 connects to the at least one 3-dimensional printing assembly chamber 682 through the aseptic connection of the secondary subchambers 654 and 684 and the tertiary subchambers 672 and 688 as previously described.

The at least one 3-dimensional printing chamber assembly 682 may be utilized to form a scaffolding and combine it with a biological product as described in U.S. Pat. No. 9,505,173 "Single-Use biological 3-dimensional Printer" and U.S. patent application Ser. No. 14/927,848 "Manufacturing within a Single-Use Container". At least one printer head 692 for the at least one 3-dimensional printing assembly chamber 682 may dispense biological material onto a scaffolding formed from at least one structural printer head 694 and/or an alternative printer head 696 that may dispense at least one metered drug product. In other examples 3D printing, biological 3D printing, CNC subtractive manufacturing, vacuum forming, injection molding, membrane pleating, laser cutting, and/or ultrasonic welding may take place within the sterile, single-use containers as further described in U.S. patent application Ser. No. 14/927,848 "Manufacturing within a Single-Use Container". In this example the printer heads 692, 694, 696 are in a fixed position within the tertiary subchamber 672, where the printer tray 698 moves along an at least 3-axis framework in a gantry 700 below within the primary subchamber 686.

The at least one robotic manipulation chamber 702 may comprise a primary subchamber 706, a secondary subchamber 704 and a tertiary subchamber 710. The at least one 3-dimensional printing assembly chamber 682 connects to the at least one robotic manipulation chamber 702 through the aseptic connection 707 of the primary subchambers 682 and 706, the secondary subchambers 684 and 704 and the tertiary subchambers 688 and 710 as previously described. The aseptic connection 707 of the primary subchambers 682 and 706 is to allow the at least one robotic arm 708 access to the printer tray 698 for manipulation of the at least one 3-dimensional printed product.

The at least one robotic arm 708 within the primary subchamber 706 is formed from sterilizable plastic materials and utilizes at least one hydraulic, pneumatic, magnetic, and/or direct drive to power and control the arm as further described in U.S. patent application Ser. No. 14/927,848 "Manufacturing within a Single-Use Container". In this example the at least one robotic arm 708 may move through the aseptic connection 707 to pick up the printer tray 698 with the at least one 3-dimensional printed product, package the at least one 3-dimensional printed product, and move the at least one packaged 3-dimensional printed product through the transfer hatch assembly 712 and into a sterile external transfer bag 714 for removal from the assembly and sterile delivery.

Figure 6:
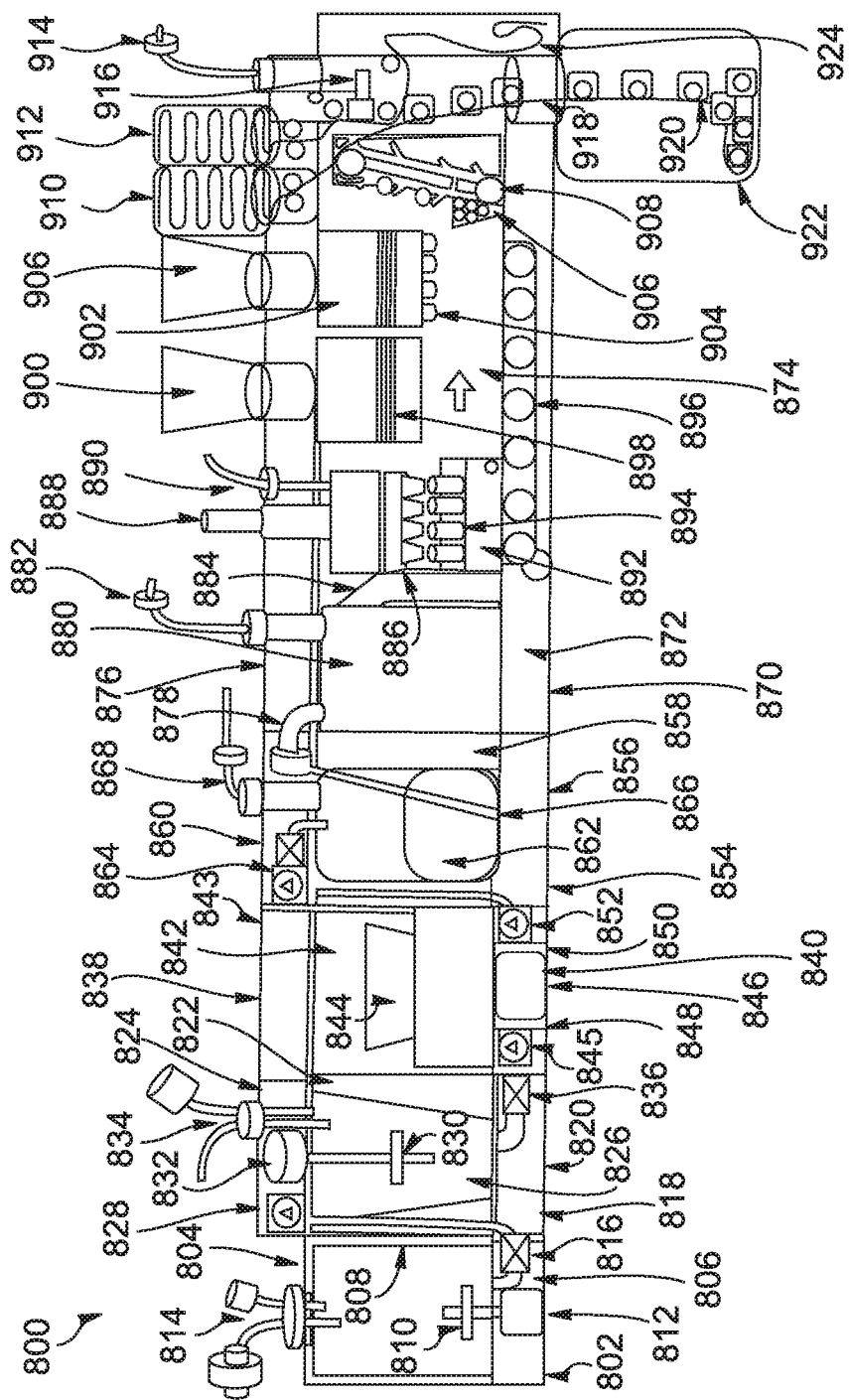
FIG. 6 illustrates an example of a manufacturing system for the upstream and downstream processing of a biological material within a network of single-use containers for the custom manufacture of Fecal Microbiota Transplant capsules.

FIG. 6 illustrates an example of a manufacturing system for the upstream and downstream processing of a biological material within a network of single-use containers for the custom manufacture of Fecal Microbiota Transplant capsules.

This manufacturing system offers a customizable platform for performing manufacturing processes which are challenging with the current tools of the biopharmaceutical industry. One of those challenges is the treatment of *Clostridium difficile* infections. The Centers for Disease Control and Prevention (CDC) in a 2011 study has estimated that the annual number of cases of *C. difficile* infections in the United States was 453,000 cases per year, with 29,300 associated deaths (https://www.cdc.gov/media/releases/2015/p0225-*clostridium-difficile*.html). Treatments using Fecal Microbiota Transplants have shown promise for treating patients with *C. difficile* infections, but conventional biomanufacturing setups with traditional stainless steel and/or single-use equipment have been unable to address this issue through standardized processing. The difficulty with current processing healthy donor fecal material for transplant has to do with the consistency of manufacturing techniques due to the wide variability of the healthy donor source material, the highly varied bacterial load within each source material sample, the requirements to separate the healthy bacteria from the donor sample limiting the killing of bacteria during processing, and the lack of consistent validated post-usage sterilization techniques for equipment and components which were in contact with the donor source material.

Fecal Microbiota Transplants have additionally been studied for treatments as varied as obesity, Crohn's disease, inflammatory bowel syndrome, diabetes, and depression. The US Food and Drug Administration announced that it would regulate fecal transplants as drugs requiring standardized manufacturing processes, which are safer alternatives to current stool banks using donor material. Enema, endoscopy, sigmoidoscopy, colonoscopy, and oral capsules full of freeze dried stool are all delivery methods that lead to successful outcomes for the patients. The complexity of the intestinal microbiome, the attempts to standardize the transplantable material, and the cleaning validations for processing equipment have slowed down progress on use of this treatment method.

This example shows a network of single-use chambers 800 for customizable biomanufacturing of Fecal Microbiota Transplant (FMT) material. The network of single-use chambers 800 may comprise one or more flexible walls made from a single-use film material, one or more rigid walls made from plastic, or a combination of at least one flexible wall and at least one rigid wall. The network of single-use chambers 800 comprises individualized single-use chambers, each with its own functionality required for the processing of a biological material internally to the network.

In this example the network of single-use chambers 800 includes but is not limited to at least one of the following chambers: a mixing assembly chamber 802, a bioreactor assembly chamber 818, a centrifugation assembly chamber 838, a fluid storage assembly chamber 854, and a freeze drying, pelletizing, encapsulation, and blister packaging chamber 870. All or some of the components and assemblies of the single-use chamber 800 may be sterilized using an approved sterilization method.

Each of the individualized chambers within the network of single-use chambers 800 may be vented using at least one vent filter assembly (not shown), which may comprise a plurality of sterilizing and/or non-sterilizing grade vent filters. The at least one vent filter assembly (not shown) maintains a sterilized air space within the individual chambers and/or within the network of single-use chambers 800. Any sterilizing grade filters from the at least one vent filter assembly (not shown) may be integrity testable to ensure sterility within the individual chambers and/or within the network of single-use chambers 800. Each of the individualized chambers may be aseptically connected to one another to form a network of single-use chambers 800 as previously described. Each of the individualized chambers within the network of single-use chambers 800 and/or subchambers may be leak testable using a leak testing device, such as a Sartocheck® 4Plus Bag Tester, to perform a leak test to check for potential punctures and/or mechanical tears on the assembly.

The at least one mixing assembly chamber 802 may be utilized to mix media, nutrient rich broths, and buffers to support the growth of at least one biological material in the at least one bioreactor chamber assembly 818. The mixing assembly chamber 802 may contain at least one internal envelope 808 within a primary subchamber 804, wherein the envelope 808 holds the fluid volume for mixing. The mixing assembly chamber 802 may comprise at least one mixing device within the at least one envelope 808, such as an impeller 810 that may connect to at least one motor assembly 812 within a secondary subchamber 806. The mixing shaft assembly with the at least one impeller 810 may comprise a plurality of impeller shapes and designs. The mixing assembly chamber 802 may comprise at least one external assembly 814 for the input of sterile material and/or the sterile venting of the at least one internal envelope 808. All other individualized chambers within the network of single-use chambers 800 may contain a similar external assembly 814.

In this example the mixing assembly chamber 802 connects to the at least one bioreactor chamber assembly 818, which comprises a primary subchamber 822, a secondary subchamber 820 and a tertiary subchamber 824, through the aseptic connection of the secondary subchambers 806 and 820 as previously described. The aseptic connection may include a fluid connection to the internal part of the mixing assembly chamber 802, in particular the at least one envelope 808, and/or a fluid line from the at least one envelope 808.

The mixing assembly chamber 802 may contain at least one valve 816, so that, when the valve 816 is in an open state, the fluid material may be pumped out of the internal envelope 808 from the mixing assembly chamber 802 to the at least one bioreactor assembly chamber 818 through at least one length of tubing. The at least one length of tubing may use at least one pump 828, which in this example is residing in the tertiary subchamber 824 of the at least one bioreactor assembly chamber 818, to pump fluid from the at least one internal envelope 808 of the at least one mixing assembly chamber 802 into an internal bioreactor envelope 826 internal to the primary subchamber 822 of the at least one bioreactor assembly chamber 818.

The at least one internal bioreactor envelope 826 may comprise at least one mixing device, such as an impeller 830, which may connect to at least one motor assembly 832 within the tertiary subchamber 824. The at least one bioreactor assembly chamber 818 may contain a heating element (not shown) that may provide thermal regulation of the bioreactor for optimal cell growth. The heating element (not shown) may utilize recirculation of a heated fluid, an electric heater jacket, a heated coil, and/or forced hot air in the region of the bioreactor assembly chamber 818. In the case of bacterial fermentation a chiller (not shown) may be utilized to maintain a constant temperature. At least one of the chambers within the network of single-use chambers 800 may be thermally regulated by at least one external assembly (not shown).

The bioreactor assembly chamber 818 may comprise at least one external assembly 834 for the inoculation of material and/or for the venting the internal bioreactor envelope 826. The inoculation material may contain a suspension of a donor fecal sample, which may be from a reference donor sample, and/or a combination of a plurality of bacterial isolates which have been confirmed to be beneficial for the intended treatments. The internal bioreactor envelope 826 may comprise at least one valve 836, such that, when the valve 836 is in an open state, the biological fluid material may be pumped out through at least one length of tubing.

In this example the bioreactor assembly chamber 818 connects to the at least one centrifugation assembly chamber 838, which comprises a primary subchamber 842, a secondary subchamber 840 and a tertiary subchamber 843, through the aseptic connection of the secondary subchambers 820 and 840 as well as the tertiary subchambers 824 and 843 as previously described.

The fluid biological harvest material from the bioreactor assembly chamber 818 may undergo further processing utilizing at least one processing method such as centrifugation, filtration, crossflow filtration, ultrafiltration, membrane adsorption, column chromatography, and/or concentration.

In this example the biological harvest material undergoes processing by centrifugation using a single-use centrifugation assembly chamber 838. The single-use centrifugation assembly 844 within the centrifugation assembly chamber 838 may be utilized for harvest clarification and/or concentration and washing of the harvest material. In this example the biological harvest material is pumped in using a pump 845 within the secondary subchamber 840. The single-use centrifugation assembly 844 within the primary subchamber 842 may comprise a plurality of single-use centrifugal cells (not shown), an internal rotor assembly (not shown), an internal fluid assembly (not shown) to supply fluid material from the bioreactor assembly chamber 818 into the single-use centrifugal cells as well as external fluid for rinsing, fluid lines (not shown) for removing and collecting waste products, and a rigid covering assembly (not shown) to protect the other components within the centrifugation chamber 838 from the high rotational speed in the interior of the single-use centrifugation assembly 844. The centrifugation motor assembly 846 is within the secondary subchamber 840.

The centrifugation assembly chamber 844 may utilize a single-use centrifugation platform e.g. from kSep® Systems, wherein a plurality of single-use chambers are filled with the fluid containing the biological material from the bioreactor assembly chamber 818 and rotated at a high speed using a rotor assembly as previously described.

In this example the biological harvest material for Fecal Microbiota Transplant (FMT) may be washed with repeated rinses of ethanol, a saline solution, and/or other buffer solution for resuspension and washing. The internal fluid assembly (not shown) may consist of a plurality of tubing lines that may supply the single-use centrifugal cells (not shown) with fluids and remove waste products from the cells. In this example at least one tubing inlet line 848 is fluidly connected to an external source and supplies the washing fluid to the single-use centrifugal cells (not-shown) while at least one waste outlet line 850 is fluidly connected to an external container that collects the waste fluid and is treated prior to disposal. The tubing lines (not shown) may be expertly positioned with a rotational joint (not shown) to prevent the tubing lines from becoming tangled during centrifugation.

As mentioned, the single-use centrifugation assembly 844 may comprise a rigid covering assembly, which may be made of a rigid, sterilizable (preferably gamma-irradiatable) plastic material to protect other components internal to the centrifugation assembly 844. While the single-use centrifugal chambers (not-shown), the internal rotor assembly (not shown), the internal fluid assembly (not shown), and the rigid covering assembly (not shown) are discarded, the external motor assembly (not shown) may be reusable.

Depending on where the desired fluid biological harvest material is located after centrifugation, either the dense pelletized material or the supernatant fluid may be collected for further processing. Dense materials may be resuspended in a fluid buffer to provide as a fluid suspension to undergo further processing. The fluid biological harvest material may be flushed with a series of rinses using buffers and/or concentrated by removing non-essential fluid during processing.

The fluid biological harvested material from the single-use centrifuge assembly 844 may be pumped out using a pump 852 for further processing. In this example the centrifugation assembly chamber 838 connects to the at least one fluid storage assembly chamber 854, which comprises a primary subchamber 858, a secondary subchamber 856 and a tertiary subchamber 860, through the aseptic connection of the secondary subchambers 840 and 856 as well as the tertiary subchambers 843 and 860 as previously described.

The filtrate of the biological harvest material may be stored in the at least one fluid storage assembly chamber 854 that contains within the primary subchamber 858 at least one internal container 862, which may be made from a rigid, non-deformable, sterilizable (preferably gamma irradiatable) plastic. The at least one internal container 862 may comprise at least one valve 864 that is in an open state during filling and in a closed state during transfer of the material utilizing a pneumatic drive method. At least one external assembly 868 containing at least one vent filter may vent the at least one internal container 862 during filling with a fluid. At least one pneumatic airline may be connected to the at least one external assembly 868 that enables a fluid connection from the exterior to the interior of the single-use chamber 854, in particular to the interior container 862. The pneumatic airline may supply a sterile air pressure source to drive the filtrate of the collected biological harvest material through the dip tube 866 within the internal container 862 to undergo further processing.

In this example the collected biological harvest material flows up the dip tube 866 into at least one length of tubing 878 into the at least one freeze drying, pelletizing, encapsulation, and blister packaging chamber 870, which comprises a primary subchamber 874, a secondary subchamber 872 and a tertiary subchamber 876. The at least one fluid storage assembly chamber 854 connects to the at least one freeze drying, pelletizing, encapsulation, and blister packaging chamber 870 through the aseptic connection of the secondary subchambers 856 and 872 and the tertiary subchambers 860 and 876 as previously described.

The at least one freeze drying, pelletizing, encapsulation, and blister packaging chamber 870 may be a single chamber or may comprise a plurality of individualized chambers depending on the processing requirements. In this example the primary subchamber 874 of the at least one freeze drying, pelletizing, encapsulation, and blister packaging chamber 870 contains the freeze drying assembly 880, which may evaporate the volatile suspension solution, such as ethanol, from the centrifuged biological harvest material, leaving a powdered material which is spread out and frozen utilizing a chiller element (not shown). The chiller may be supplied with sterile chilled air through an external assembly 882 containing a sterilizing grade air filter. The external assembly 882 may contain a pressurized airline that may serve as a drive mechanism for controlling the internal mechanics of the freeze drying assembly 880.

The powdered frozen harvest material from the freeze drying assembly 880 is transported down a chute 884 into a holding tray 886 with a plurality of divots and holes. The divots within the holding tray 886 collect the powdered frozen harvest material and provide the sizing for the pellets to be inserted into the capsules. The holes may be opened after compression of the pellets, which may drop through the holes into the halves of capsules 894, using guides (not shown) within the capsule transport assembly 892. The pelletization compression assembly 888 utilizes an external drive mechanism to compress the powdered frozen harvest material on the holding tray 886 into pellets of a predetermined sizing. In some examples a coating such as gelatin or other coating material may be fluidly injected onto the pellets from the pelletization compression assembly 888 using external fluid line 890. This may provide a coating around the pellets so that they are able to pass through the acidity within the stomach before completely dissolving or to prevent the patient from perceiving a bad taste if the capsule wall is compromised.

The halves of the capsules 894 are placed in the capsule transport assembly 892 when the assembly is under a capsule placement assembly 898 that uses a hopper 900 with capsule halves. The capsule halves in the hopper 900 may be manufactured under sterile conditions and/or sterilized after manufacture. The capsule halves drop into the capsule placement assembly 898, where they are oriented so that the open end is facing up and so that they are in the same spacing and positioning as the capsule openings in the capsule transport assembly 892.

When the capsule transport assembly 892 makes the initial pass, the capsule halves are dropped into the capsule openings using guides (not shown). The capsule transport assembly 892 moves along a track within the primary subchamber 874 using a conveyor belt drive assembly 896 within the secondary subchamber 872 with an external drive mechanism (not shown) and a connection within the primary subchamber 874. This capsule transport assembly 892 moves along this conveyor belt drive assembly 896 track, makes an initial stop to pick up the capsule halves and has the pelletized biological material dropped into the open capsule halves. The capsule transport assembly 892 then moves to a capsule compression assembly 902, which closes the filled capsule with the other half 904 of a capsule assembly and compresses it to lock it into place.

The capsule compression assembly 902 uses a hopper 906 with capsule halves. The capsule halves in the hopper 906 may be manufactured under sterile conditions and/or sterilized after manufacture. The capsule halves drop into the capsule compression assembly 902, where they are oriented so that the open end is facing down and so that they are in the same spacing and positioning as the filled capsules in the capsule transport assembly 892.

The capsule transport assembly 892 then moves to the end of the track where the assembly may invert and/or open to drop the filled capsules into a filled capsule storage container 906. The filled capsules in the filled capsule storage container 906 are transported by a vertical conveyor 908 to a blister packaging assembly where at least one side of the blister packaging is supplied from a storage container 910. The filled capsule is inserted, and at least one second side of the blister packaging supplied from a storage container 912 overlays the capsule and is sealed utilizing heat, compression, or other action from a blister packaging piston 916. The blister packed capsules 920 are fed through a transfer hatch assembly 918 into a storage container 922 for collection. The waste material from the blister packaging operation are fed into a waste storage container 924 for removal when filled.

The customized platform utilizing a network of single-use chambers described in this example may be applied to other bioprocessing manufacturing setup including but not limited to vaccine production into sterile syringes and viral vectors production for delivery of CRISPR sequences.

External assemblies may be utilized to control, regulate, and monitor the networks of single-use chambers described heretofore. The network of single-use chambers may operate on a benchtop or within a facility on their own with support equipment and utilities connected to each individual chamber in the network of single-use chambers. Alternatively, the network of single-use chambers may be arranged in a container assembly where the network of single-use chambers, the supporting equipment, and the utility connections are arranged and controlled in a more manageable setup.

Such a container assembly may comprise an enclosure configured to accommodate at least one single-use chamber for performing an operation comprising at least one of generation and handling of a biological material. The enclosure may have flexible walls or rigid walls or a combination thereof, wherein the walls may be transparent. The enclosure may also be sterilizable. The enclosure may have an internal volume sufficient for accommodating a whole network of chambers configured to perform upstream and downstream processing of a biological material. The enclosure may comprise an internal structure such as including scaffolds, platforms and/or poles, so that the single-use chambers may be orderly arranged and supported within the enclosure.

The enclosure may comprise at least one supporting equipment module, wherein the at least one supporting equipment module is configured to be operatively coupled to the at least one single-use chamber to support the operation of the at least one single-use chamber. The at least one supporting equipment module comprises at least one of the following:
- at least one connection to supplying units;
- at least one connection to waste containers;
- at least one drive mechanism for driving devices contained in the at least one single-use chamber;
- at least one component configured to perform tasks in preparation for the operation of the at least one single-use chamber;
- at least one component configured to perform tasks after the operation of the at least one single-use chamber.

The at least one supporting equipment module may, thus, have a fluid and/or mechanical connection to the single-use chambers. The connection methods between the supporting equipment module and the single-use chambers may be the same previously discussed for the connections between chambers or subchambers.

If one or more of the single-use chambers comprise subchambers, the secondary and/or tertiary subchambers may serve as intermediary between the primary subchambers and the supporting equipment modules.

The container assembly may further comprise at least one supplying unit, such as a sterile filtered water storage tank and a compressed air storage tank. Exemplarily, the supplying units may not be within the enclosure but rather on the outside of it.

A modular arrangement of the at least one supporting equipment module and of the at least one single-use chamber is selectively mountable in one configuration of a plurality of possible configurations. In other words, the single-use chambers and the supporting equipment modules may be freely arranged within the enclosure and the arrangement is not fixed but can modified according to necessity. This means that all components within the enclosure may be moved from a first position to a second position and the relative location of a component with respect to another one can be modified. Further, both the supporting equipment modules and the single-use chambers are modules in the modular system, i.e. functional smaller parts that can be used in connection with one other according to a plurality of different designs.

The enclosure may further comprise an access opening configured to allow the modular arrangement of the at least one supporting equipment module and of the at least one single-use chamber to be modified.

In some examples, the enclosure may be positioned on a rigid base and the rigid base may be formed by a plurality of displaceable elements. In other words, the base may be modular, so that its composition may be adjusted according to which/how many single-use chambers and/or supporting equipment modules are located on a specific part of the base.

Exemplarily, the rigid base may comprises at least one wheel so as to make the container assembly movable. The enclosure may, thus, be positioned e.g. on a cart, skid, and/or mobile trailer.

The container assembly may further comprises a controlling device configured to control the at least one supporting equipment module and the at least one single-use chamber. The controlling device may control all the components inside the enclosure, thus simplifying the controlling process. In particular, the controlling device may control the operations that take place within the network of single-use chambers combined with the supporting equipment modules. These operations may include but are not limited to data acquisition, data analysis, power supplying, water supplying, centrifugation, mixing, perfusion, opening and closing of valves, activation and deactivation of pumps, venting, filtering and dispensing.

Figure 7:
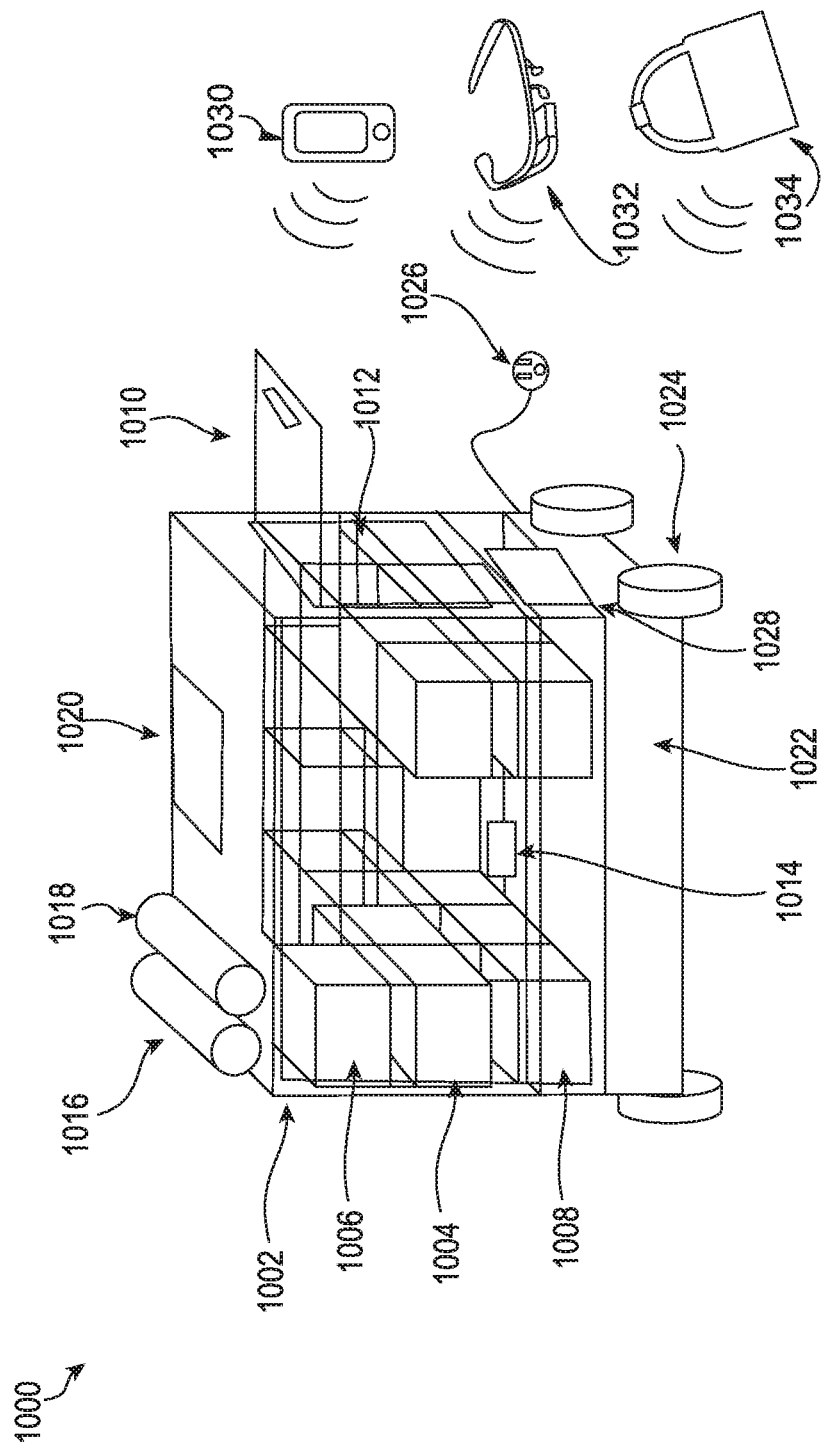
FIG. 7 illustrates an example of a container assembly for single-use containers, which includes supporting equipment and supplying units.

FIG. 7 illustrates an example of a container assembly for single-use containers, which includes supporting equipment and supplying units.

In this example a modular container controlling assembly 1000 may comprise an enclosure with at least one rigid wall 1002, which may contain at least one single-use chamber 1004 arranged in a particular layout or pattern. Exemplarily the enclosure may contain also a second single-use chamber 1006 connected from above to the single-use chamber 1004, in order to allow gravity to drain a fluid material into the single-use chamber 1004 below. The single-use chamber 1006 may comprise a mixing container that drains a thoroughly mixed media into a bioreactor vessel internal to the single-use chamber 1004 below.

The enclosure may contain at least one supporting equipment module 1008 to control, regulate, and monitor the conditions of the single-use chamber 1004 to which it is connected. The at least one supporting equipment module 1008 may control the mechanical drive mechanisms which support mixers, pumps, centrifuges and other mechanical devices inside the at least one single-use chamber 1004. The at least one supporting equipment module 1008 may connect the at least one single-use chamber 1004 to utilities such as fluids, compressed gases, electricity, and/or storage containers such as waste containers.

The utilities connected to the modular container controlling assembly 1000 may be connected through an external connection to a utility existing within the room it is placed in and/or may be self-contained and stored on the modular container controlling assembly 1000 itself. In this example a sterile filtered water storage tank 1016 and a compressed air storage tank 1018 are locally stored on the modular container controlling assembly 1000. In exemplary embodiments the modular container controlling assembly 1000 may contain an air handler and filtration assembly 1020 to provide a classified airspace within the interior in case any of the single-use chambers 1004 and 1006 is punctured or contains a leak.

The single-use chambers 1004 and 1006 and the at least one supporting equipment module 1008 may be arranged, connected, setup, disconnected, and removed through access doors and/or hatches on the modular container controlling assembly 1000. In this example there is a hatch 1010 on the side of the modular container controlling assembly 1000 that provides an access opening 1012 to the interior of the enclosure. The enclosure may comprise an additional access door 1014 that may be opened to access single-use chambers 1004 and 1006 and at least one supporting equipment module 1008. In exemplary embodiments the modular container controlling assembly 1000 may be large enough for a person to walk into and insert, arrange, and/or remove the at least one single-use chamber 1004 and 1006 and at least one supporting equipment module 1008. The setup of the single-use chambers may be changed depending on the specific kind of processing to be conducted within, and accordingly the modular supporting equipment module 1008 may be moved and positioned to fit the needs of the individual chambers within the network of single-use chamber setups. The modular container controlling assembly 1000 may contain a rigid base 1022 that may be modular in itself so that elements of the base 1022 may be moved around for different weights and loading configurations.

In this example the rigid base comprises at least one wheel 1024 to be able to move and/or transport the modular container controlling assembly 1000 with the single-use chambers 1004 and 1006. The modular container controlling assembly 1000 may contain a power supply including a wall plug, a battery, a generator, a solar panel, and/or other electrical generation assembly. An independent power supply 1026 may be useful in rural areas and/or in field areas where access to steady power may not be accessible.

An operator may control the modular container controlling assembly 1000 with a display screen and controller input device 1028. The display screen and controller input device 1028 may serve as a programmable logic controller (PLC) for controlling the batch recipes, the data/sensor analysis, and operation of the modular container controlling assembly 1000. Additionally and/or alternatively the modular container controlling assembly 1000 may wirelessly communicate with an external device such as at least one mobile device 1030, at least one augmented reality device 1032, at least one virtual reality device 1034, and/or at least one mixed reality device (not shown).

The previous examples demonstrated the use of a network of individualized single-use chambers for small-scale to mid-scale biomanufacturing with a focus on personalized medicine. In other examples the network of individualized single-use chambers may be miniaturized to a microfluidic scale for the purposes of micro-scale biomanufacturing and/or for multi-step configurable diagnostic testing.

FIGS. 8A and 8B illustrate an example of a miniaturized container assembly for single-use containers.

FIG. 8A is a front view of a mobile device 1100 for the upstream and downstream processing of a biological material. The mobile device 1100 may contain a rigid body 1102 for holding the at least one individual single-use chamber 1108. Exemplarily, a plurality of single-use chambers 1108 may be connected to form a network of single-use chambers. The mobile device 1100 may contain at least one modular supporting equipment module 1104 that may connect to the at least one individual single-use chamber 1108.

As explained for the supporting equipment module 1008 of FIG. 7, the at least one supporting equipment module 1104 may contain the mechanical drive mechanisms that support mixers, pumps, centrifuges and other mechanical devices inside the at least one individual single-use chamber 1108. The at least one modular supporting equipment module 1104 may also contain a connection to a circuit of utility lines 1106 including fluids, compressed gases, electricity, and/or storage containers such as waste containers.

The at least one modular supporting equipment module 1104 may contain an attachment mechanism (not shown) to securely connect the at least one individual single-use chambers 1108 to the mobile device 1100. The at least one modular supporting equipment module 1104 may be removed individually or in combination with other modules and replaced with another layout of connections to a circuit of utility lines 1106 as the processing requires.

The mobile device 1100 may contain at least one input device 1110 to control, regulate, and monitor the operation of the at least one individual single-use chambers 1108, the at least one modular supporting equipment module 1104, and/or the at least one circuit of utility lines 1106. In other examples a display device (not shown) may be provided on the mobile device 1100 and/or the mobile device may be controlled and the data may be displayed on at least one external device (not shown), such as a computer laptop or workstation, at least one mobile device (not shown), at least one augmented reality device (not shown), at least one virtual reality device (not shown), at least one mixed reality device (not shown), and/or other display device (not shown).

FIG. 8B is a side view of a mobile device 1112 for the upstream and downstream processing of a biological material, which may include all or some of the features of the mobile device 1100 described with reference to view A.

The mobile device 1112 may contain a rigid body 1114 for holding the individual single-use chambers 1118 and 1124, which may be connected to form a network of single-use chambers. The at least one modular supporting equipment module 1116 may be removed individually or in combination with other modules and replaced with another layout of connections to a circuit of utilities lines as the processing requires.

The individual single-use chamber 1124 may connect to the at least one modular supporting equipment module 1116 and/or the at least one individual single-use chamber 1118 adjacent to it. The individual single-use chambers 1118 and 1124 may be aseptically connected to each other through the primary subchamber 1124, secondary subchamber 1122, and/or tertiary subchamber (not shown) as previously described. The individual single-use chambers 1118 and 1124 may additionally or alternatively be aseptically connected to the at least one modular supporting equipment module 1116 through connection 1126.

The individual single-use chambers 1118 and 1124 may conduct upstream and downstream bioprocessing as previously described. Additionally or alternatively the mobile device 1112 may be utilized for multi-step configurable diagnostic testing. In a multi-step configurable diagnostic testing, a sample from a patient such as a fluid sample (blood, urine, fecal material, cerebral spinal fluid, seminal fluid, etc.) and/or a solid sample such as from a biopsy, aspiration, and/or an extracted mass, is given. The sample undergoes several processing steps such as being aseptically inserted into a bioreactor assembly where the material is grown under regulated conditions, the material is later harvested, flushed, and purified through filtration or other means. The material may then be dispensed onto a diagnostic membrane coated with an analyte such as an antibody specific for binding where the material may be precisely measured by an electronic sensing device. As an example this process may be utilized for the culture and microbial analysis of a patient sample that is cultured within a bioreactor assembly and later dispensed into a plurality of containers (not shown) that undergo screening with a series of antibiotics and/or metered doses of drug products to determine the best course for patient treatment. Such a technique would allow for a limited patient sample to be grown under controlled conditions to provide as source material for testing a plurality of potential treatment options. A similar technique could be utilized to culture a tumor and/or cancer biopsy from a patient, which could be aseptically inserted into a bioreactor assembly where the material is grown under regulated conditions, and later dispensed into a plurality of chambers and/or containers (not shown) that undergo screening with a series of metered doses of drug products, such as chemotherapeutic drug products, immunogenic drug products, genetically engineered drug products (CRISPR, viral vectors, etc.), or through physical manipulation such as radiation treatments to determine the susceptibility of the biopsied tumor and the best course of action for patient treatment.

The physical components of the mobile device 1112 may include at least one power device, preferably a rechargeable battery 1128; at least one barrier 1130 to prevent fluid from leaking into the battery compartment; at least one container for input materials 1132, such as sterile water, nutrient rich media, a buffer, or other fluid material; at least one container for pressurized gas 1134 such as nitrogen and/or compressed air; at least one container for the collection of the biological processed product 1136; and at least one container for the collection of waste products 1138 including fluid wastes. All of the containers 1132, 1134, 1136 and 1138 may be modular and removable from the mobile device assembly. The mobile device 1112 may fluidly connect, preferably aseptically connect, the containers 1132, 1134, 1136 and 1138 to the circuit of utility lines within the at least one modular supporting equipment module 1116.

The electronic components of the mobile device 1112 may include at least one circuit board 1148, which may be coated to prevent damage from a fluid leak; at least one processing device 1140 for processing batch protocols and recipes; at least one memory storage device 1142 for storing batch protocols and recipes as well as storing monitoring, sensor, and/or measurement data; at least one communication device 1144 for transmitting data wirelessly 1150 to an external device; and at least one input device 1146 to input commands into the mobile device.

LIST OF REFERENCE SIGNS

100 Single-use chamber
102 Flexible film wall
104 Transfer hatch assembly
106 Mixing assembly
108 Impeller
110 External assembly
112 Filter assembly
114 Vent filter assembly
116 Pump
118 Tubing
120 Bioreactor assembly
122 Impeller
124 External assembly
126 Inoculation port
128 Vent filter assembly
130 Valve
132 Pump
134 Perfusion Assembly
136 Pump
138 Aseptic connector
140 Pump
142 Single-use centrifugation assembly
144 Pump
146 Depth filter
148 Prefilter
150 Sterilizing grade filter
152 Valve
154 Internal container
155 Vent filter
156 External assembly
158 Pneumatic airline
160 Dip tube
162 Aseptic connector
164 Tubing
166 Crossflow assembly
168 Valve
170 Internal container
172 Vent filter
174 Pneumatic airline
176 Dip tube
178 Aseptic connector
180 Tubing
182 Sterile filling assembly
184 Ports
186 Sterile bags
188 Vent filter
190 Tubing clips
200 Network of single-use chambers
202 Mixing assembly chamber
204 Container and/or envelope
206 Impeller
208 External assembly
210 Vent filter assembly
212 Filter assembly
214 Transfer hatch assembly
216 Transfer hatch assembly
218 Length of tubing
220 Bioreactor assembly chamber
222 Internal bioreactor container and/or envelope
224 External assembly
225 Impeller
226 Vent filter assembly 228 Inoculation port
230 Pump
232 Length of tubing
234 Perfusion assembly chamber
236 Perfusion assembly
238 Transfer hatch assembly
240 Aseptic connection
242 Valve
244 Pump
246 Pump
248 Pump
250 Length of tubing
252 Centrifugation assembly chamber
254 Centrifugation assembly
256 Transfer hatch assembly
258 Length of tubing
260 Pump
262 Filtration assembly chamber
264 Transfer hatch assembly
268 Length of tubing
270 Depth filter
272 Prefilter
274 Final sterilizing grade filter
276 Length of tubing
278 Transfer hatch assembly
280 Transfer hatch assembly
282 Length of tubing
284 Fluid storage assembly chamber
286 Internal container
288 Vent filter
290 External assembly
292 Pneumatic airline
294 Transfer hatch assembly
296 Transfer hatch assembly
298 Dip tube
300 Crossflow purification and concentration assembly chamber
302 Crossflow purification and concentration assembly
304 Transfer hatch assembly
306 Aseptic connection
308 Length of tubing
310 Length of tubing
312 Transfer hatch assembly
314 Aseptic connection
316 Pump
318 Filling manifold
320 Filling assembly chamber
322 Transfer hatch assembly
324 Aseptic connection
326 Pump
328 Filling manifold
330 Filling assembly chamber
332 Transfer hatch assembly
334 Ports
336 Sterile bags
338 Vent filter assembly
340 Tubing clips
400 Single-use chamber
402 Primary subchamber (flexible)
404 Secondary subchamber (rigid)
406 Mixing assembly container
408 Impeller
410 Motor assembly
412 Power cable
414 External connection
416 Piping
418 Outlet piping
420 Sensor and/or measurement device
422 External connection
424 Aseptic connection assembly
426 Attachment device
428 Attachment device
450 Single-use chamber
452 Primary subchamber (flexible)
454 Secondary subchamber (rigid)
456 Tertiary subchamber (rigid)
458 Mixing assembly container
460 Impeller
462 Motor assembly
464 Power cable
466 External connection
468 Sensor and/or measurement device
470 Cable
472 External connection
474 Piping
476 Outlet piping
478 Aseptic connection assembly
480 Aseptic connection assembly
482 Attachment device
484 Attachment device
500 Single-use chamber
502 Primary subchamber (rigid)
504 Secondary subchamber (flexible)
506 Mixing assembly container
508 Impeller
510 Motor assembly
512 Power cable
514 External connection
516 Piping
518 Outlet piping
520 Sensor and/or measurement device
522 External connection
524 Aseptic connection assembly
526 Attachment device
528 Attachment device
530 Cable
550 Piping
552 Single-use chamber
554 Primary subchamber (rigid)
556 Secondary subchamber (flexible)
558 Tertiary subchamber (flexible)
560 Impeller
562 Motor assembly
564 Power cable
566 External connection
568 Sensor and/or measurement device
570 Cable
572 External connection
574 Piping
576 Outlet piping
578 Aseptic connection assembly
580 Aseptic connection assembly
582 Attachment device
584 Attachment device
600 Network of single-use chambers
602 Mixing assembly chamber
604 Primary subchamber
606 Secondary subchamber
608 Container and/or envelope
610 Impeller
612 External assembly
614 Motor assembly
616 Valve
618 Bioreactor assembly chamber 620 Secondary subchamber
622 Primary subchamber
624 Tertiary subchamber
626 Internal bioreactor container and/or envelope
628 Pump
630 Impeller
632 Motor assembly
634 External assembly
636 Valve
638 Perfusion assembly chamber
640 Secondary subchamber
642 Primary subchamber
644 Tertiary subchamber
645 Pump
646 Perfusion assembly
648 Pump
650 Pump
652 Filtration assembly chamber
654 Secondary subchamber
656 Primary subchamber
658 Depth filter
660 Prefilter
662 Sterilizing grade filter
664 Valve
666 Fluid storage assembly chamber
668 Secondary subchamber
670 Primary subchamber
672 Tertiary subchamber
674 Internal container
676 Valve
678 External assembly
680 Dip tube
682 3-Dimensional printing assembly chamber
684 Secondary subchamber
686 Primary subchamber
688 Tertiary subchamber
690 3-Dimensional printer head supply line
692 Printer head
694 Printer head
696 Printer head
698 Printer tray
700 Gantry
702 Robotic manipulation chamber
704 Secondary subchamber
706 Primary subchamber
707 Aseptic connection
708 Robotic arm
710 Tertiary subchamber
712 Transfer hatch assembly
714 External transfer bag
800 Network of single-use chambers
802 Mixing assembly chamber
804 Primary subchamber
806 Secondary subchamber
808 Container and/or envelope
810 Impeller
812 Motor assembly
814 External assembly
816 Valve
818 Bioreactor assembly chamber
820 Secondary subchamber
822 Primary subchamber
824 Tertiary subchamber
826 Internal bioreactor container and/or envelope
828 Pump
830 Impeller
832 Motor assembly
834 External assembly
836 Valve
838 Centrifugation assembly chamber
840 Secondary subchamber
842 Primary subchamber
843 Tertiary subchamber
845 Pump
846 Centrifugation motor assembly
848 Tubing inlet line
850 Waste outlet line
852 Pump
854 Fluid storage assembly chamber
856 Secondary subchamber
858 Primary subchamber
860 Tertiary subchamber
862 Internal container
864 Valve
866 Dip tube
868 External assembly
870 Freeze drying, pelletizing, encapsulation, and blister packaging chamber
872 Secondary subchamber
874 Primary subchamber
876 Tertiary subchamber
878 Length of tubing
880 Freeze drying assembly
882 External assembly
884 Chute
886 Holding tray
888 Pelletization compression assembly
890 External fluid line
892 Capsule transport assembly
894 Half of capsules
896 Conveyor belt drive assembly
898 Capsule placement assembly
900 Hopper of capsule halves
902 Capsule compression assembly
904 Half of capsule assembly
906 Hopper of capsule halves
908 Vertical conveyor
910 Storage container
912 Storage container
914 External assembly
916 Blister packaging piston
918 Transfer hatch assembly
920 Blister packed capsules
922 Storage container
924 Waste storage container
1000 Container controlling assembly
1002 Rigid wall
1004 Single-use chamber
1006 Single-use chamber
1008 Supporting equipment module
1010 Hatch
1012 Access opening
1014 Access door
1016 Filtered water storage tank
1018 Compressed gas storage tank
1020 Air handler and filtration assembly
1022 Rigid base
1024 Wheel
1026 Power supply
1028 Display screen and controller input device
1030 Mobile device
1032 Augmented reality device
1034 Virtual reality device 1100 Mobile device for the upstream and downstream processing of biological material
1102 Rigid body
1104 Supporting equipment module
1106 Circuit of utility lines
1108 Single-use chamber
1110 Input device
1112 Mobile device for the upstream and downstream processing of biological material
1114 Rigid body
1116 Supporting equipment module
1118 Single-use chamber
1120 Single-use chamber
1122 Secondary subchamber
1124 Primary subchamber
1126 Connection
1128 Rechargeable battery
1130 Barrier
1132 Container for input materials
1134 Container for pressurized gas
1136 Container for the collection of biological process product
1138 Waste products container
1140 Processing device
1142 Memory storage device
1144 Communication device
1146 Input device
1148 Circuit board
1150 Transmitting data wirelessly
1200 Benchtop manufacturing setup
1202 Bioreactor control unit
1204 Single-use bioreactor
1206 Length of tubing
1208 Network of single-use chambers
1210 Centrifugation assembly chamber
1212 Secondary subchamber
1214 Pump
1216 Primary subchamber
1218 Centrifugation assembly
1220 Centrifugation motor assembly
1222 Pump
1224 Filtration assembly chamber
1226 Secondary subchamber
1228 Length of tubing
1230 Primary subchamber
1232 Depth Filter
1234 Prefilter
1236 Sterilizing grade filter
1238 Valve
1240 Fluid storage assembly chamber
1242 Secondary subchamber
1243 Length of tubing
1244 Pump
1245 Tertiary subchamber
1246 Valve
1248 Primary subchamber
1250 Internal container
1252 External assembly
1254 Pneumatic airline
1256 Dip tube
1258 Filling assembly chamber
1260 Tertiary subchamber
1262 Pump
1264 Fluid piping connection
1266 Primary subchamber
1268 Sterile bag filling manifold
1270 Secondary subchamber
1272 Single-use bags
1274 Vent filter
1276 Tubing clips

What is claimed is:

1. A system for performing upstream and downstream processing of biological material, the system comprising a single-use chamber that is connectable to a corresponding single-use chamber, the single-use chamber comprising:
a primary subchamber formed from a flexible material and containing a flexible mixing receptacle within the primary subchamber and having primary components in or on the flexible mixing receptacle that are configured to perform an operation comprising at least one of generation and handling of a biological material, the primary components including a mixing device disposed within the flexible mixing receptacle and at least one sensor mounted on the flexible mixing receptacle and communicating with an interior of the flexible mixing receptacle, the at least one sensor collecting data regarding material disposed in the flexible mixing receptacle;
a secondary subchamber formed from a rigid material and having a top wall with the primary subchamber supported thereon and side walls extending down from the top wall, the secondary subchamber containing secondary components configured to support the operation of the primary components of the single-use chamber, the secondary components including power cables and wiring, and data cables that have connections provided at the side walls of the secondary subchamber, the secondary components further including fluid lines with connectors provided at the side walls of the secondary subchamber and configured to aseptically couple the single-use chamber to the corresponding single-use chamber;
wherein the primary subchamber and the secondary subchamber are configured to be connected removably to each other so that the primary components are operatively coupled to the secondary components when the primary subchamber and the secondary subchamber are connected, the primary subchamber and the secondary subchamber further being configured to be separated from one another so that the primary components no longer are operatively coupled to the secondary components when the primary subchamber and the secondary subchamber are separated; and
attachment devices provided on the side walls of the secondary subchamber and configured for linking and holding the single-use chamber to the corresponding single-use chamber of the system.

2. The system of claim 1, wherein the primary subchamber and the secondary subchamber are configured to be sterilized respectively via first and second sterilization methods that are different from one another.

3. The system of claim 1, wherein the primary subchamber is configured to be sterilized and the secondary subchamber is configured to remain unsterilized.

4. A network of single-use chambers for performing upstream and downstream processing of biological material, the network comprising:
a plurality of single-use chambers, wherein each of the single-use chambers of the plurality of single-use chambers comprises:
a primary subchamber formed from a flexible material and containing at least one primary component configured to perform an operation comprising at least one of generating a biological material and handling the biological material, the primary subchamber further having at least one sensor collecting data regarding the biological material disposed in the primary subchamber;

a secondary subchamber formed from a rigid material and having a top wall with the primary subchamber supported thereon and side walls extending down from the top wall, the secondary subchamber containing secondary components configured to support the operation of the at least one primary component, the secondary components including power cables, wiring, and data cables that have connections provided at the side walls of the secondary subchamber, the secondary components further including fluid lines with fluid connections configured to aseptically couple each of the single-use chambers to another one of the plurality of single-use chambers;

wherein:

the primary subchamber and the secondary subchamber of each of the single-use chambers are configured to be connected removably to each other so that the at least one primary component is operatively coupled to the secondary components when the primary subchamber and the secondary subchamber are connected, the primary subchamber and the secondary subchamber further being configured to be separated from one another so that the at least one primary component no longer is operatively coupled to the secondary components when the primary subchamber and the secondary subchamber are separated;

connection lines with connectors provided at the side walls of the secondary subchamber and configured to aseptically and at least partially fluidly couple each of the single-use chambers to at least one other one of the single-use chambers;

attachment devices provided on the side walls of the secondary subchamber of each of the plurality of the single-use chambers and configured for attachment to the attachment devices provided on the side walls of the secondary subchamber of another one of the plurality of the single-use chambers for linking and holding the single-use chambers together;

each one of the single-use chambers of the plurality of single-use chambers is configured differently from each other one of the single-use chambers of the plurality of single-use chambers to perform a different step in the upstream and downstream processing of the biological material; and the at least one primary component in at least one of the single use chambers further includes a mixing device.

* * * * *